United States Patent
Möhwald et al.

(10) Patent No.: US 6,475,663 B1
(45) Date of Patent: Nov. 5, 2002

(54) COMPOSITIONS SUITABLE FOR ELECTROCHEMICAL CELLS

(75) Inventors: Helmut Möhwald, Annweiler; Gerhard Dötter; Rainer Blum, both of Ludwigshafen; Peter Keller, Spiesen-Elversberg; Stephan Bauer, Hochdorf-Assenheim; Bernd Bronstert, Otterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,076
(22) PCT Filed: Aug. 6, 1999
(86) PCT No.: PCT/EP99/05702
§ 371 (c)(1), (2), (4) Date: Feb. 1, 2001
(87) PCT Pub. No.: WO00/08068
PCT Pub. Date: Feb. 17, 2000

(30) Foreign Application Priority Data

Aug. 6, 1998 (DE) .......................... 198 35 615

(51) Int. Cl.[7] ................................. H01M 4/64
(52) U.S. Cl. ................ 429/129; 521/149; 429/304
(58) Field of Search ................. 429/129, 304; 521/149

(56) References Cited

U.S. PATENT DOCUMENTS

| | | | |
|---|---|---|---|
| 4,131,731 A | 12/1978 | Lai et al. .................. 528/370 |
| 4,241,149 A | 12/1980 | Labes et al. ................ 429/50 |
| 5,073,611 A | 12/1991 | Rehmer et al. ............. 526/208 |
| 5,098,973 A | 3/1992 | Kozuka et al. ............. 526/282 |
| 5,128,386 A | 7/1992 | Rehmer et al. .............. 522/35 |
| 5,296,318 A | 3/1994 | Gozdz et al. .............. 429/192 |
| 5,420,204 A | 5/1995 | Valet et al. ............... 525/125 |
| 5,429,891 A | 7/1995 | Gozdz et al. .............. 429/192 |
| 5,558,911 A | 9/1996 | Blum ...................... 427/517 |
| 5,587,253 A | * 12/1996 | Gozdz et al. .............. 429/192 |
| 5,622,792 A | 4/1997 | Brochu et al. ............. 429/192 |
| 6,225,010 B1 | * 5/2001 | Hamano et al. ............ 429/306 |

FOREIGN PATENT DOCUMENTS

| | | |
|---|---|---|
| CA | 2250107 | 10/1997 |
| DE | 44 33 290 | 3/1996 |
| DE | 196 12 769 | 10/1997 |
| DE | 196 53 631 | 6/1998 |
| DE | 198 19 752 | 11/1999 |
| EP | 377 199 | 7/1990 |
| EP | 0 395 990 | 11/1990 |
| EP | 526 399 | 2/1993 |
| EP | 666 607 | 8/1995 |

OTHER PUBLICATIONS

K. Mura Kami in Chem. High Polymers (Japan) 7 (1950) pp. 188–193.

Eisle et al. "Mécanisme de photoréticulatio de polymères cotenant le motif dicyclopehtadiène en présemce et an absence de benzophénone" Macromol. Chem. Phys. vol. 197 (1996) pp. 1731–1756.

Steinberg "Organoboron Chemistry" Chapter 5 (1964) pp. 217–261.

Armand et al. "Fast Ion Transport in Solids" (1979) pp. 131–136.

Ullmanns Encyklopädie der technischen Chemie, vol. 4, Band 19, (1980) pp. 62–65.

Morrison et al. "Homolytic Bond Dissociation Energies, KCAL/MOL$^a$" Organic Chemistry Sixth Edition (1992).

Ullmanns Encyclopedia of Industrial Chemical Fifth Edition, vol. A3 (1985) pp. 343–397.

* cited by examiner

Primary Examiner—Steven P. Griffin
Assistant Examiner—M. Wills
(74) Attorney, Agent, or Firm—Keil & Weinkauf

(57) ABSTRACT

A composition comprising:
(a) from 0 to less than 1% by weight of a pigment (I) having a primary particle size of from 5 nm to 100 $\mu$m which is a solid Ia or a compound Ib which acts as cathode material in electrochemical cells or a compound Ic which acts as anode material in electrochemical cells or a mixture of the solid Ia with the compound Ib or the compound Ic,
(b) more than 99 to 100% by weight of a polymeric material (II) which comprises:
(IIa) from 1 to 100% by weight of a polymer or copolymer (IIa) containing reactive groups (RG) on the chain in terminal and/or lateral positions which are capable of crosslinking reactions in the presence of heat and/or with UV radiation, and
(IIb) from 0 to 99% by weight of at least one polymer or copolymer (IIb) which contains no reactive groups (RG).

9 Claims, 2 Drawing Sheets

COMPOSITIONS SUITABLE FOR ELECTROCHEMICAL CELLS

BACKGROUND OF THE INVENTION

The present invention relates to compositions which are suitable, inter alia, for electrochemical cells with electrolytes containing lithium ions; to their use, for example, in and as solid electrolytes, separators and electrodes; to solid electrolytes, separators, electrodes, sensors, electrochromic windows, displays, capacitors and ion-conducting films which contain a composition of this type, and to electrochemical cells containing such solid electrolytes, separators and/or electrodes.

Electrochemical, in particular rechargeable cells are known in general terms, for example from "Ullmann's Encyclopedia of Industrial Chemistry", $5^{th}$ Edn., Vol. A3, VCH Verlagsgesellschaft mbH, Weinheim, 1985, pages 343–397.

Of these cells, Aithium batteries and lithium ion batteries occupy a special position, in particular as secondary cells, owing to their high specific energy storage density.

Cells of this type contain in the cathode, as described, inter alia, in the above passage from "Ullnann", lithiated manganese, cobalt, vanadium or nickel mixed oxides, as, in the stoichiometrically simplest case, can be described as $LiMn_2O_4$, $LiCoO_2$, $LiV_2O_5$ or $LiNiO_2$.

These mixed oxides react reversibly with compounds which can incorporate lithium ions into their lattice, for example graphite, with removal of lithium ions from the crystal lattice, where the metal ions such as manganese, cobalt or nickel ions, can be oxidized in the latter. This reaction can be utilized in an electrochemical cell for current storage by separating the compound which takes up the lithium ions, ie. the anode material, and the lithium-containing mixed oxide, ie. the cathode material, by an electrolyte, through which the lithium ions migrate from the mixed oxide into the anode material (charging operation).

The compounds which are suitable for reversible storage of lithium ions are usually fixed lo drain electrodes by means of a binder.

During charging off the cell, electrons flow through an external voltage source and lithium cations flow through the electrolyte to the anode material. During use of the cell, the lithium cations flow through the electrolyte, whereas the electrons flow through a working resistance from the anode material to the cathode material.

In order to avoid a short-circuit within the electrochemical cell, an electrically insulating, but lithium cation-permeable layer is located between the two electrodes. This can be a so-called solid electrolyte or a conventional separator.

Solid electrolytes and separators consist, as is known, of a support material in which a lithium cation-containing compound which is capable of dissociation is incorporated in order to increase the lithium ion conductivity, and further additives, such as solvents, are usually also incorporated.

U.S. Pat. Nos. 5,296,3181 and 5,429,891, for example, propose a copolymer of vinylidene fluoride and hexafluoropropene as support material. However, the use of high-resistance (co)copolymers of this type is afflicted with a number of disadvantages.

Polymers of this type are not only expensive, but can also only be dissolved with difficulty. Furthermore, owing to their comparatively low lithium cation conductivity, thy increase the resistance of the cell, and consequently the electrolyte, which usually consists of a lithium cation-containing compound, such as $LiPF_6$, $LiAsF_6$ or $LiSbF_6$, and an organic solvent, such as ethylene carbonate or propylene carbonate, has already been added to the insulating layer during production (U.S. Pat. Nos. 5,296,318 and 5,429,891). In addition, polymers of this type can only by processed with, for example, high proportions of plasticizers, for example di-n-butyl phthalate, and pyrogenic silicas, which are added in order firstly to ensure adequate film-formation and cohesion of the electrolyte layer and bondability to the electrode layers and secondly ensure adequate conductivity and permeability for lithium cations. The plasticizer must, before the batteries are used, be separated quantitatively from the laminate comprising anode, solid electrolyte or separator layer and cathode layer in an extraction step which is expensive and extremely difficult on an industrial scale.

WO 97/37397 relates inter alia, to a mixture Ia comprising a mixture IIa consisting of
- a) from 1 to 95% by weight of a solid III, preferably a basic solid III having a primary particle size of from 5 nm to 20 μm, and
- b) from 5 to 99% by weight of a polymeric composition IV obtainable by polymerization of
  - b1) from 5 to 100% by weight, based on the composition IV, of a condensation product V of
    - a) at least one compound VI which is capable of reacting with a carboxylic acid or a sulfonic acid or a derivative or a mixture of two or more thereof, and
    - b) at least 1 mol per mole of the compound VI, of a carboxylic acid or sulfonic acid VII containing at least one free-radical-polymerizable functional group, or of a derivative thereof or of a mixture of two or more thereof, and
  - b2) from 0 to 95% by weight, based on the composition IV, of a further compound VIII having a mean molecular weight (number average) of at least 5000 containing polyether segments in the main or side chain, where the proportion by weight of the mixture Ia in the mixture Ia is from 1 to 100% by weight.

Although the systems described therein already have excellent properties, in particular when used in electrochemical cells, such as, for example, excellent short-circuit resistance high mechanical stability and good processing properties, use of these systems usually requires that the actual foil production or photocrosslinking step in the production of, for example, cast foils, be carried out under inert-gas conditions.

A further improved system for use in electrochemical cells, in particular a composition which can be processed better, ie. with avoidance of inert-gas conditions, is described in DE-A 198 19 752. This relates to a composition comprising:
- (a) from 1 to 99% by weight of a pigment (I) having a primary particle size of from 5 nm to 100 μm which is a solid Ia or a compound Ib which acts as cathode material in electrochemical cells or a compound Ic which acts as anode material in electrochemical cells or a mixture of the solid Ia with the compound Ib or the compound Ic,
- (b) from 1 to 99% by weight of a polymeric material (II) which comprises:
  - (IIa) from 1 to 100% by weight of a polymer or copolymer (IIa) containing reactive groups (RG) on the chain in terminal and/or lateral positions which are capable of crosslinking reactions in the presence of heat and/or with UV radiation, and (IIb) from 0 to 99% by weight of at least one polymer or copolymer (IIb) which contains no reactive groups (RG).

In more detailed investigations, it has now been found that a further-improved composition of the type under discussion here and a highly porous membrane can also be obtained if the pigment content of the composition described in DE-A 198 19 752 is significantly reduced.

SUMMARY OF THE INVENTION

Accordingly, the present invention relates to a composition comprising:

(a) from 0 to less than 1% by weight of a pigment (I) having a primary particle size of from 5 nm to 100 μm which is a solid Ia or a compound Ib which acts as cathode material in electrochemical cells or a compound Ic which acts as anode material in electrochemical cells or a mixture of the solid Ia with the compound Ib or the compound Ic, (b) more than 99 to 100% by weight of a polymeric material (II) which comprises:

(IIa) from 1 to 100% by weight of a polymer or copolymer (IIa) containing reactive groups (RG) on the chain in terminal and/or lateral positions which are capable of crosslinking reactions in the presence of heat and/or with UV radiation, and (IIb) from 0 to 99% by weight of at least one polymer or copolymer (IIb) which contains no reactive groups (RG).

The novel composition above has the following surprising properties:

Although the pigment only contains a small proportion of a pigment (I), or none at all, the composition is highly active and mechanically stable; it is highly suitable as an ion-conducting polymer electrolyte system, particularly suitable for use in lithium ion batteries; even without or with a small proportion of filler, a highly porous membrane which is suitable for use in lithium ion batteries can be obtained;

the small proportion of pigment (I) or the total omission thereof enables the production of transparent foils, for example solid electrolyte foils, which are highly suitable for use in electrochromic windows;

the photocrosslinking step in the production of the cast foil does not require inert-gas conditions;

the mechanical properties of the foils resulting from the composition can be controlled from hard/brittle to soft/elastic simply through the composition of the polymer (IIa);

the presence of the polymer (IIb) means that the resultant foil is thermoplastic and can be laminated directly onto the active electrodes without addition of further auxiliaries and/or at room temperature by means of pressure;

the mechanical properties of the composition are further improved compared with those having a higher proportion of pigment; the polymeric material in the composition is chemically inert and does not need to be stored in the absence of light and air.

DETAILED DESCRIPTION OF THE INVENTION

Figure 1:
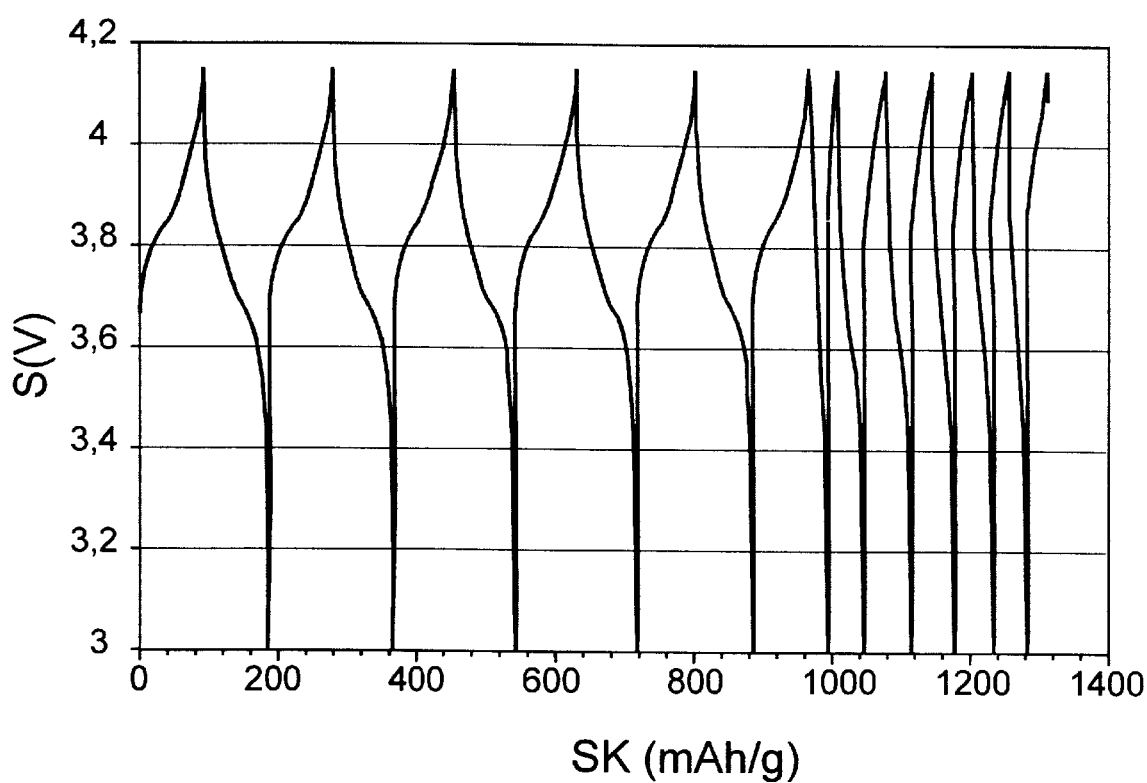
FIG. 1 shows the results of cycling (voltage 4.15V) the cells in accordance with Example 1.

The invention is now described in detail:

The pigment I can be a solid Ia selected from the group consisting of an inorganic solid, preferably an inorganic basic solid, selected from the group consisting of oxides, mixed oxides, carbonates, silicates, sulfates, phosphates, amides, imides, nitrides and carbide of the elements from main group I, II, III or IV or sub-group IV of the Periodic Table, a polymer selected from the group consisting of polyethylene, polypropylene, polystyrene, polytetrafluoroethylene, polyvinylidene fluoride, polyamides and polyimides; a solid dispersion comprising a polymer of this type; glass powder, glass nanoparticles, for example Monosper® (Merck), glass microparticles, for example Spheriglas® (Potters-Ballotini), nanowhiskers and a mixture of two or more thereof, giving a composition which can be used as solid electrolyte and/or separator.

Particular mention may be made by way of example of the following: oxides, for example silicon dioxide, aluminum oxide, magnesium oxide or titanium oxide, mixed oxides, for example of the elements silicon, calcium, aluminum, magnesium or titanium, silicates, for example ladder silicates, chain silicates, sheet silicates and framework silicates, for example talc, pyrophyllite, muscovite, phlogopite, amphiboles, nesosilicates, pyroxenes, sorosilicates, zeolites, feldspars, wollastonite, in particular hydrophobicized wollastonite, mica and phyllosilicates; sulfates, for example alkali metal and alkaline earth metal sulfates; carbonates, for example alkali metal and alkaline earth metal carbonates, for example calcium carbonate, magnesium carbonate or barium carbonate, or lithium carbonate, potassium carbonate or sodium carbonate; phosphates, for example apatites; amides; imides; nitrides; carbides; polymers, for example polyethylene, polypropylene, polystyrene, polytetrafluoroethylene, polyvinylidene fluoride, polyamides, polyimides or other thermoplastics, thermosets or microgels, crosslinked polymer particles, for example Agfaperl®, solid dispersions, in particular those containing the abovementioned polymers, and mixtures of two or more of said solids.

The inert solid Ia employed in accordance with the invention may furthermore be inorganic solids which conduct Li ions, preferably an inorganic basic solid which conducts Li ions.

The following may be mentioned: lithium borates, for example $Li_4B_6O_{11}*xH_2O$, $Li_3(BO_2)_3$, $Li_2B_4O_7*xH_2O$, $LiBO_2$, where x can be a number from 0 to 20; lithium aluminates, for example $Li_2O*Al_2O_3*H_2O$, $Li_2Al_2O_4$, $LiAlO_2$; lithium aluminosilicates, for example lithium-containing zeolites, feldspars, feldspathoids, phyllosilicates and inosilicates, and in particular $LiAlSi_2O_6$ (spodumene), $LiAlSi_4O_{10}$ (petullite), $LiAlSiO_4$ (eucryptite), mica, for example $K[Li,Al]_3[AlSi]_4O_{10}(F—OH)_2$, $K[Li,Al,Fe]_3[AlSi]_4O_{10}(F—OH)_2$; lithium particular those in fiber, sheet or tube form, in particular those having the general formula $Li_{2/z}O*Al_2O_3*xSiO_2*yH_2O$, where z corresponds to the valency, x is from 1.8 to about 12 and y is from 0 to about 8; lithium carbides, for example $Li_2C_2$ or $Li_4C$; $Li_3N$; lithium oxides and mixed oxides, for example $LiAlO_2$, $Li_2MnO_3$, $Li_2O$, $Li_2O_2$, $Li_2MnO_4$, $Li_2TiO_3$; $Li_2NH$; $Li_2NH_2$; lithium phosphates, for example $Li_3PO_4$, $LiPO_3$, $LiAlFPO_4$, $LiAl(OH)PO_4$, $LiFePO_4$, $LiMnPO_4$; $Li_2CO_3$; lithium silicates in ladder, chain, sheet and framework form, for example $Li_2SiO_3$, $Li_2SiO_4$ and $Li_6Si_2$; lithium sulfates, for example $Li_2SO_4$, $LiHSO_4$, $LiKSO_4$; and the Li compounds mentioned as compound Ib, the presence of conductive black being excluded if it is used as solid Ia; and mixtures of two or more of the abovementioned Li ion-conducting solids.

The solids Ia are preferably hydrophobicized solids Ia, further preferably hydrophobicized compounds of the abovementioned type.

Particularly suitable here are basic solids. For the purposes of the present invention, the term basic solids is taken to mean those whose mixture with a liquid, water-containing diluent which itself has a pH of at most 7 has a higher pH than this diluent.

The solids should advantageously be substantially insoluble in the liquid used as electrolyte and should be electrochemically inert in the battery medium.

The invention furthermore relates to a composition in which the pigment I is a compound Ib which acts as cathode material in electrochemical cells and is selected from the group consisting of $LiCoO_2$, $LiNiO_2$, $LiNi_xCo_yO_2$, $LiNi_xCo_yAl_2O_2$, with $0<x,y,z \leq 1$, $Li_xMnO_2$ ($0<x \leq 1$), $Li_xMn_2O_4$ ($0<x \leq 2$), $Li_xMoO_2$ ($0<x \leq 2$), $Li_xMnO_3$ ($0<x \leq 1$), $Li_xMnO_2$ ($0<x \leq 2$), $Li_xMn_2O_4$ ($0<x \leq 2$), $Li_xV_2O_4$ ($0<x \leq 2.5$), $Li_xV_2O_3$ ($0<x \leq 3.5$), $Li_xVO_2$ ($0<x \leq 1$), $Li_xWO_2$ ($0<x \leq 1$), $Li_xWO_3$ ($0<x \leq 1$), $Li_xTiO_2$ ($0<x \leq 1$), $Li_xTi_2O_4$ ($0<x \leq 2$), $Li_xRuO_2$ ($0<x \leq 1$), $Li_xFe_2O_3$ ($0<x \leq 2$), $Li_xFe_2O_4$ ($0<x \leq 2$), $Li_xCr_2O_3$ ($0<x \leq 3$), $Li_xCr_3O_4$ ($0<x \leq 3.8$), $Li_xV_3S_5$ ($0<x \leq 1.8$), $Li_xTa_2S_2$ ($0<x \leq 1$), $Li_xFeS_2$ ($0<x \leq 1$), $Li_xFeS_2$ ($0<x \leq 1$), $Li_xNbS_2$ ($0<x \leq 2.4$), $Li_xMoS_2$ ($0<x \leq 3$), $Li_xTiS_2$ ($0<x \leq 2$), $Li_xZrS_2$ ($0<x \leq 2$), $Li_xNbSe_2$ ($0<x \leq 3$), $Li_xVSe_2$ ($0<x \leq 1$), $Li_xNiPS_2$ ($0<x \leq 1.5$), $Li_xFePS_2$ ($0<x \leq 1.5$), $LiNi_xB_{1-x}O_2$ ($0<x<1$), $LiNi_xAl_{1-x}O_2$ ($0<x<1$), $LiNi_xMg_{1-x}O_2$ ($0<x<1$), $LiNi_xCo_{1-x}VO_4$ ($1 \geq x \geq 0$), $LiNi_xCo_yMn_zO_2$ ($x+y+z=1$), $LiFeO_2$, $LiCrTiO_4$, $Li_aM_bL_cO_d$ ($1.15 \geq a > 0$; $1.3 \geq b + c 0.8$; $2.5 \geq d \geq 1.7$; M=Ni, Co, Mn; L=Ti, Mn, Cu, Zn, alkaline earth metals), $LiCu_y^{II}Cu_y^{III}Mn_{(2-(x+y))}O_4$ ($2 > x+y \geq 0$), $LiCrTiO_4$, $LiGa_xMn_{2-x}O_4$ ($0.1 \geq x \geq 0$), polycarbon sulfides of the general structure $-[C(S_x)]_n-$, $V_2O_5$, a mixture of two or more thereof, and a mixture of the compound Ib with the solid Ia, and the composition additionally comprises from 0.1 to 20% by weight, based on the total amount of component I and II, of conductive black, having a composition which can be used, in particular, as cathode.

The invention furthermore relates to a composition in which the pigment I is a compound Ic which acts as anode material in electrochemical cells and is selected from the group consisting of lithium, a lithium-containing metal alloy, micronized carbon black, natural and synthetic graphite, synthetically graphitized coaldust, a carbon fiber, titanium oxide, zinc oxide, tin oxide, molybdenum oxide, tungsten oxide, titanium carbonate, molybdenum carbonate, zinc carbonate, $Li_xM_ySiO_z$ ($1>x \geq 0.1 \geq y \geq 0$, $z>0$), $Sn_2BPO_4$, conjugated polymers, for example polypyrroles, polyanilines, polyacetylenes, polyphenylenes, lithium metal compounds $Li_xM$, for example those in which M=Sn, Bi, Sb, Zn, Cd or Pb and $5 \geq x \geq 0$; Li—Sn—Cd, CdO, PbO, a mixture of to or more thereof, and a mixture of the compound Ic with the solid Ia, and the composition additionally comprises up to 20% by weight, based on the total amount of components I and II, of conductive black, giving a composition which can be used, in particular, as anode.

Particularly suitable pigments are those which have a primary particle size of from 5 nm to 20 μm, preferably from 0.01 to 10 μm, in particular from 0.1 to 5 μm, the stated particle sizes being determined by electron microscopy. The melting point of the pigments is preferably above the usual operating temperature of electrochemical cells, a melting point of above 120° C., in particular above 150° C., having proven particularly suitable.

The pigments here can be symmetrical with respect to their external shape, ie. have a height:width:length size ratio (aspect ratio) of approximately 1 and be in the form of beads, granules, approximately round structures, but also in the form of any desired polyhedra, for example as cuboids, tetrahedra, hexahedra, octahedra or as bipyramides, or can be distorted or asymmetric, ie. have a height:width:length size ratio (aspect ratio) which is not equal to 1 and be in the form, for example, of needles, asymmetric tetrahedra, asymmetric bipyramids, asymmetric hexahedra or octahedra, platelets, disks or fibrous structures. If the solids are in the form of asymmetrical particles, the abovementioned upper limit for the primary particle size relates to the smallest axis in each case.

The composition according to the invention comprises from 0 to less than 1% by weight, preferably from 0 to 0.5% by weight, further preferably 0% by weight, of a pigment I and more than 99 to 100% by weight, preferably from 99.5 to 100%, further preferably 100% by weight, of the polymeric material II.

This polymeric material II comprises from 1 to 100% by weight of at least one polymer IIa containing reactive groups (RG) on the chain in terminal and/or internal positions which are capable of crosslinking reactions in the presence of heat and/or with UV radiation, and from 0 to 99% by weight of at least one polymer or copolymer (IIb) which contains no reactive groups (RG).

The polymers IIa can in principle be any polymers which can be crosslinked in the presence of heat and/or with high-energy radiation, preferably with UV light, which contain reactive groups (RG), preferably reactive groups RGa or RGb or RGa and RGb, on the chain in terminal and/or lateral positions via which the polymers can crosslink with thermal and/or radiation activation.

The polymer IIa is further preferably a polymer which contains at least one first reactive group RGa band at least one group RGb which is different from RGa and is coreactive with RGa, in each case on the chain in terminal and/or lateral positions, where, on average of all polymer molecules, at least one RGa and one RGb are present.

The polymer IIa may furthermore be formed from a mixture of a plurality of polymers some containing only RGa and the others containing only RGb.

The polymer IIa may furthermore be formed from a mixture of a plurality of polymers some containing RGa and the others containing only RGb and further polymers containing both RGa and RGb.

In general, the polymer IIa is formed from a uniform polymer class, preferably from the polyacrylate class. However, blends of various polymer classes are also possible.

The polymer IIa covers both polymeric and oligomeric substances and mixtures of polymeric and oligomeric substances.

The oligomeric and/or polymeric basic structure of the polymers IIa covers known polymers, as built up, for example, by —C—C— linkages, which may also be double and/or triple bonds, and by ether, ester, urethane, amide, imide, imidazole, ketone, sulfide, sulfone, acetal, urea, carbonate and siloxane linkages.

The oligomeric or polymeric basic structure may furthermore have a linear, branched-chain, cyclic or dendrimeric structure.

The polymers IIa used in accordance with the invention can be obtained by polymerization, polyaddition or polycondensation of monomer units containing RGa and/or RGb in addition to the groups via which the polymer build-up takes place, with the formation of polymers Ia which are functionalized in accordance with the invention as early as during polymer preparation.

The polymers IIa according to the invention can furthermore be obtained by polymer-analogous reaction of functional polymers with compounds containing RGa and/or Rqb and at least one further group which is able to react with the functional groups of the oligomeric or polymeric basic structure.

It is furthermore possible to incorporate one of the functional groups RGa and/or RGb as early as during polymer preparation and then to introduce the other RG into the finished polymer by polymer-analogous functionalization.

Groups RGa are groups having structures which are capable of hydrogen abstraction under high-energy radiation, preferably UV light, in the triplet-excited state (photoinitiator groups of the Norrish II type which are known from the literature). Such structures are known to the person skilled in the art from photochemistry. The corresponding acrylate (derivative) compounds which have structures of this type are furthermore listed here. Further details regarding these compounds are given in U.S. Pat. No. 5,558,911, which is incorporated into this application by way of reference regarding its contents in this respect. Other monomers, oligomers or polymers having structures RGa of this type can of course also be employed in accordance with the invention.

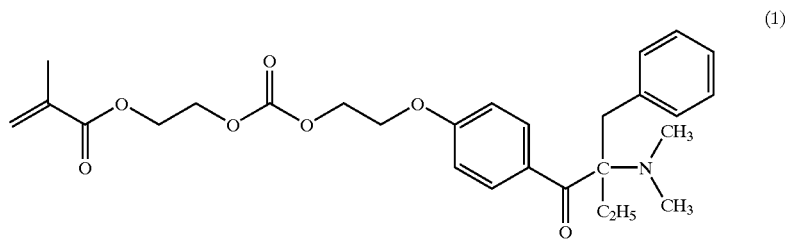
(1)

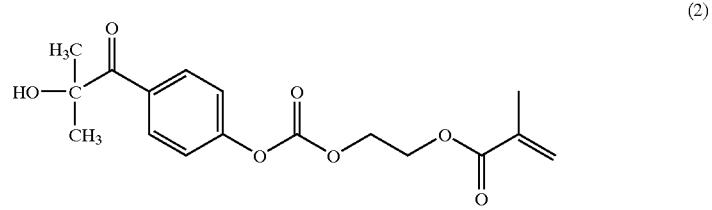
(2)

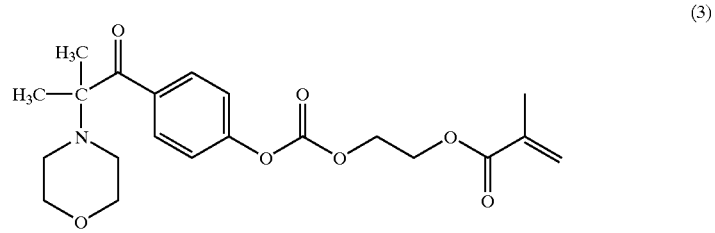
(3)

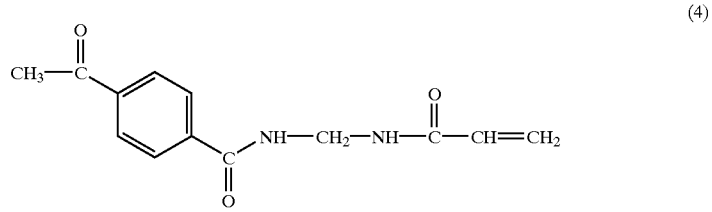
(4)

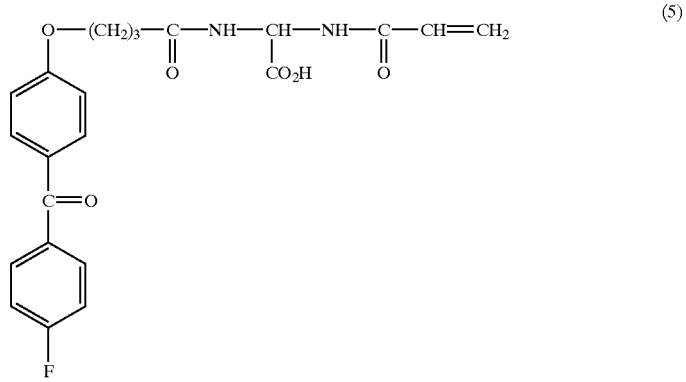
(5)

(6)
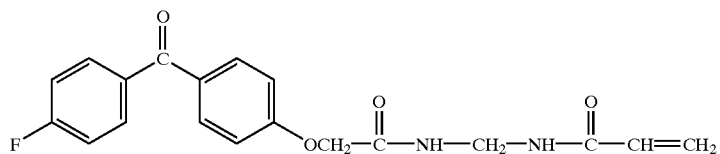
(7)
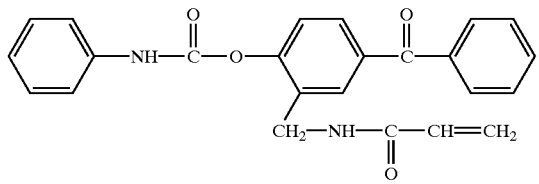
(8)
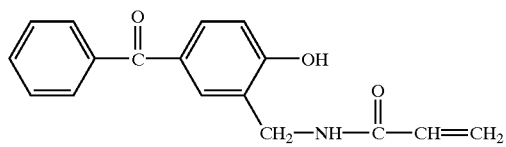
(9)
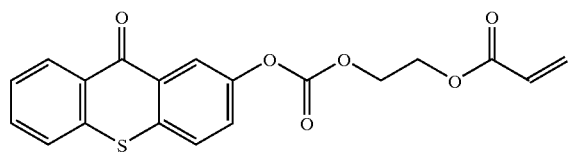
(10)
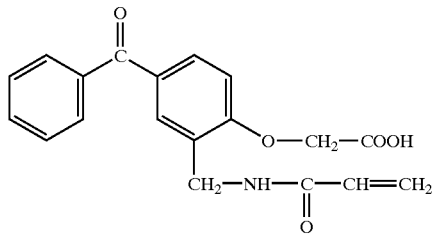
(11)
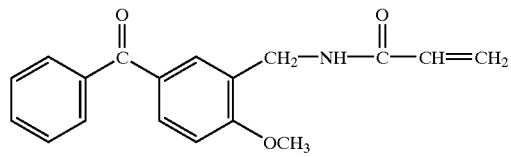
(12)
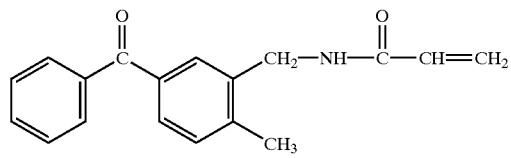
in which,
$R^6$ is —$CH_3$ or —$C_6H_5$,
$R^7$ is H or —$CH_3$,
(13)
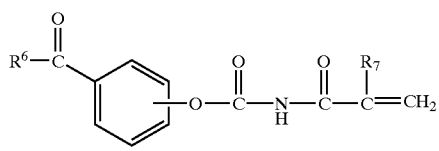

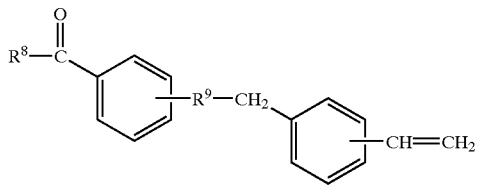
in which,
$R^8$ is —$C_nC_{2n+1}$, where n = 1 to 3, or —$C_6H_5$
$R^9$ is —O—, —$\overset{\overset{O}{\|}}{C}$—O—, —$\overset{R^{10}}{\underset{}{N}}$— OR —$\overset{\oplus}{N}(R^{11})_2$—
$R^{10}$ is —H or —$C_nH_{2n-1}$, where n = 1 to 8, and
$R^{11}$ is —$C_nH_{2n-1}$, where n = 1 to 4
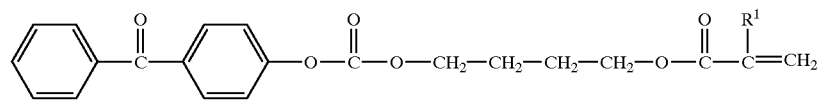
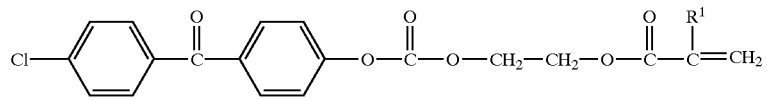
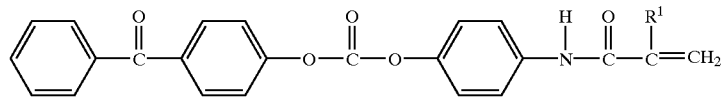
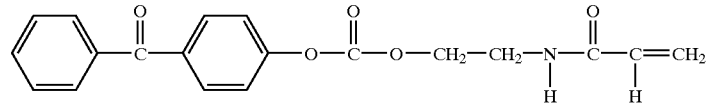
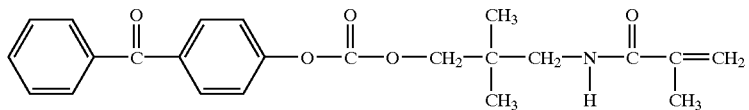
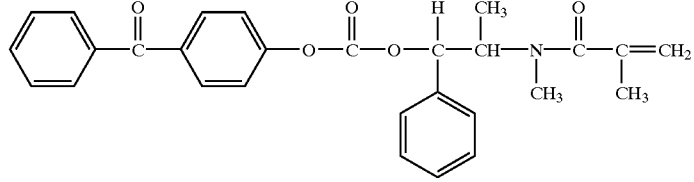
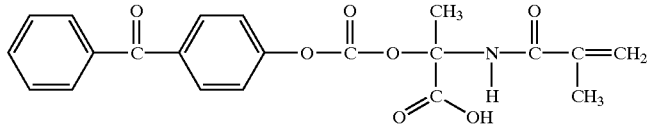
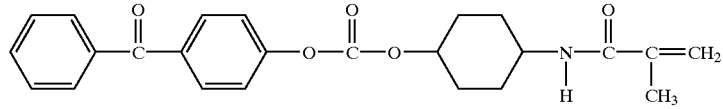
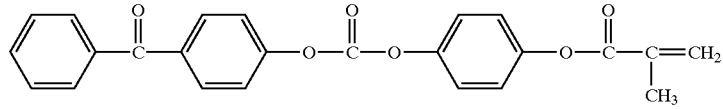

-continued
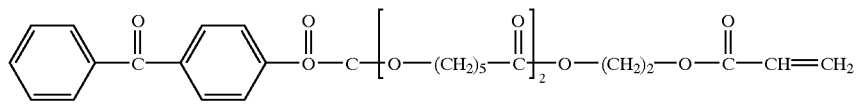
(24)
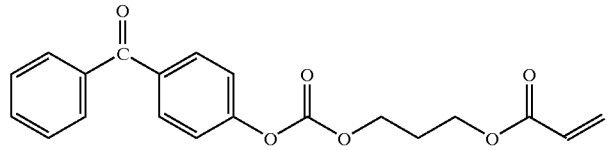
(25)
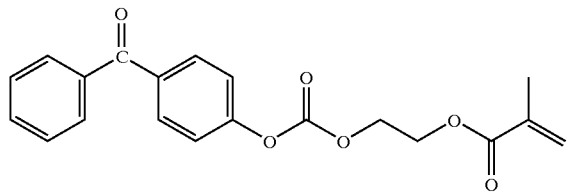
(26)
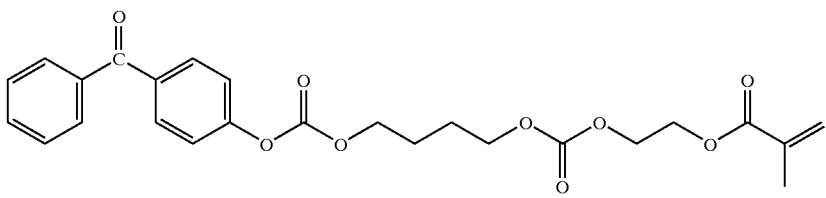
(27)
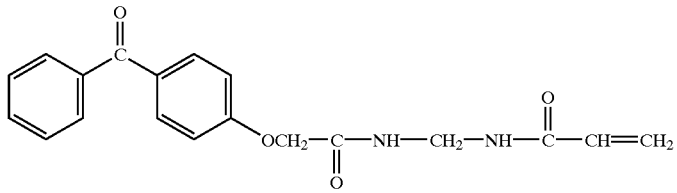
(28)
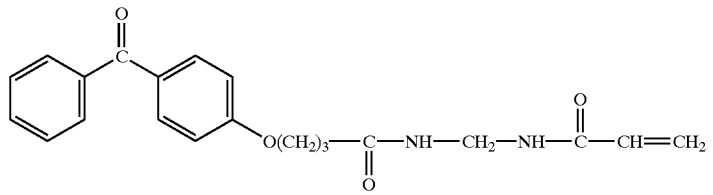
(29)
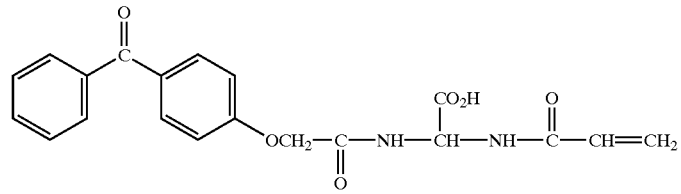
(30)
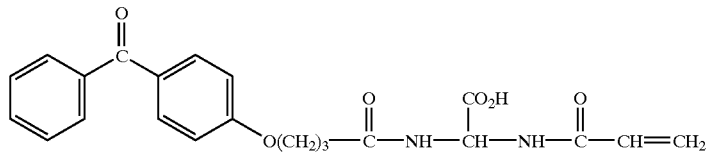
(31)

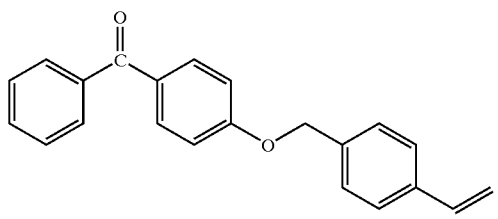
(32)
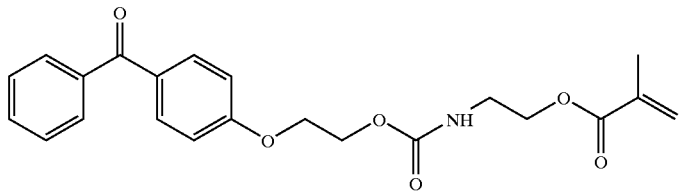
(33)
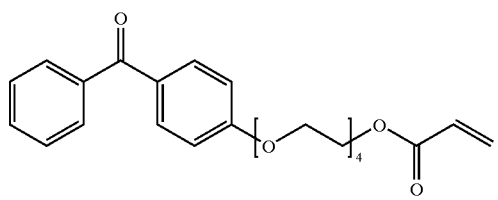
(34)
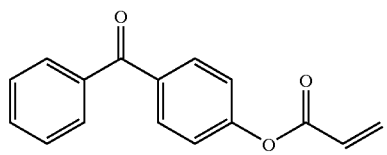
(35)
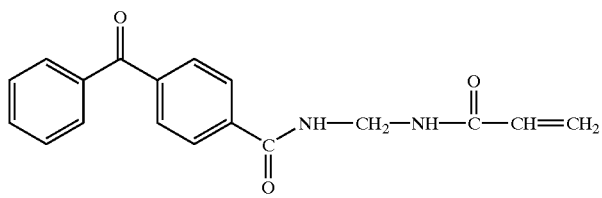
(36)
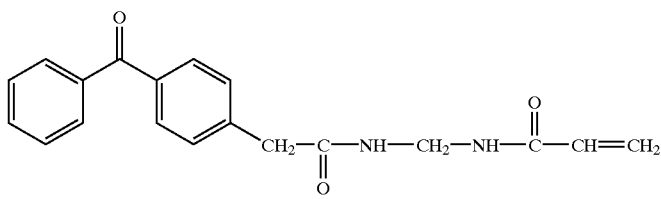
(37)
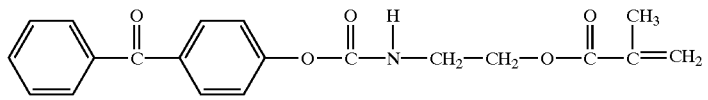
(38)
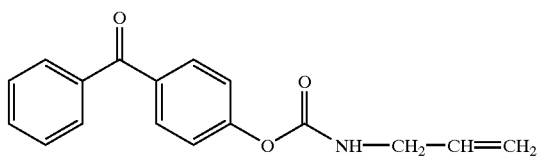
(39)
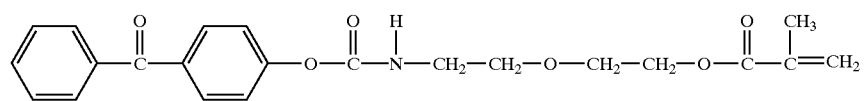
(40)

-continued

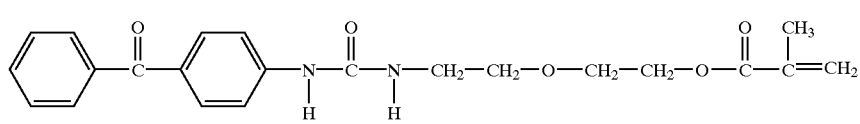

(41)

where $R^1$=H or $CH_3$.

The concomitant use of such RGa acrylates enables, for example, acrylate copolymers which have been functionalized with RGa in a manner according to the invention to be obtained very simply by copolymerization with further acrylates.

Furthermore, basic polymers containing, for example, amino groups, but containing no RGa groups, can easily be functionalized with RGa via a Michael addition of such RGa acrylates.

RGa are preferably benzophenone groups. Particularly high UV reactivity is achieved in polyacrylates with benzophenone derivatives in which the benzophenone group is bonded to the main polymer chain via a spacer group. Particularly preferred polyacrylates are obtainable by copolymerization of acrylates of the formulae 24 to 26 and of the formula 34. A further inexpensive and preferred way of introducing RGa into the polymers is the reaction of hydroxybenzophenones, preferably 4-hydroxybenzophenone, with the epoxide groups of a polymer, preferably the addition reaction of 4-hydroxybenzophenone with polyacrylates with glycidyl (meth)acrylate components. A further elegant method is the reaction of an adduct comprising one mole of diisocyanate with one mole of 4-hydroxybenzophenone with a polymer containing free hydroxyl groups.

A preferred method of introducing RGa into polyesters comprises the concomitant use of benzopheonecarboxylic acids or benzophenonecarboxylic anhydrides in the polycondensation or the reaction or esterification of polymers containing hydroxyl groups, epoxide groups, isocyanate groups and/or amino groups with benzophenonecaboxylic acids or benzophenonecarboxylic anhydrides.

RGb groups are groups which are able to interact with excited Norrish II photoinitiator groups. An interaction of this type which is particularly known to the person skilled in the art is hydrogen transfer to the Norrish II structure, resulting in the formation of free radicals, both in the case of the H donor and in the case of the abstracting Norrish II structure. Direct crosslinking of the polymers is possible via a free-radical combination. Furthermore, initiation of a free-radical-initiated polymerization of for example, photopolymerizable functional groups RGb, for example meleate, fumarate, (meth)acrylate, allyl, epoxide, alkenyl, cycloalkenyl, vinyl ether, vinyl ester, vinylaryl and cinnamate groups, by the photochemically produced free radicals is also possible.

Preference is given to RGb groups which interact as H donor with RGa, ie. systems containing no double bonds. An intrinsic advantage of the system is the low interference sensitivity of these systems since they have reduced reactivity, compared with saturated UV systems, to the other constituents of the overall formulation. However, this of course does not exclude the (concomitant) use of unsaturated substances, which is an optimization task in individual cases. H-donor groups are known to the person skilled in the art of photochemistry. These are in principle group which contain hydrogens of low bonding energy, in particular groups containing hydrogen atoms having a bonding energy of less than 397 kJ/mol.

Data on bonding energy are known from the literature and are given, for example, in Morrison, Bobert Thornton, Organic Chemistry, Table: Homolytic Bond Dissociation Energies, on the inside of the cover, in Library of Congress Cataloging-in-Publication Data ISBN0-205-08453-2, 1997, by Allyn and Bacon, Inc., A Division of Simon & Schuster, Newton, Massachusetts, USA.

Examples are amine, furfuryl, tetrahydrofurfuryl, isobornyl and isoalkyl compounds and compound containing groups of the following structures:

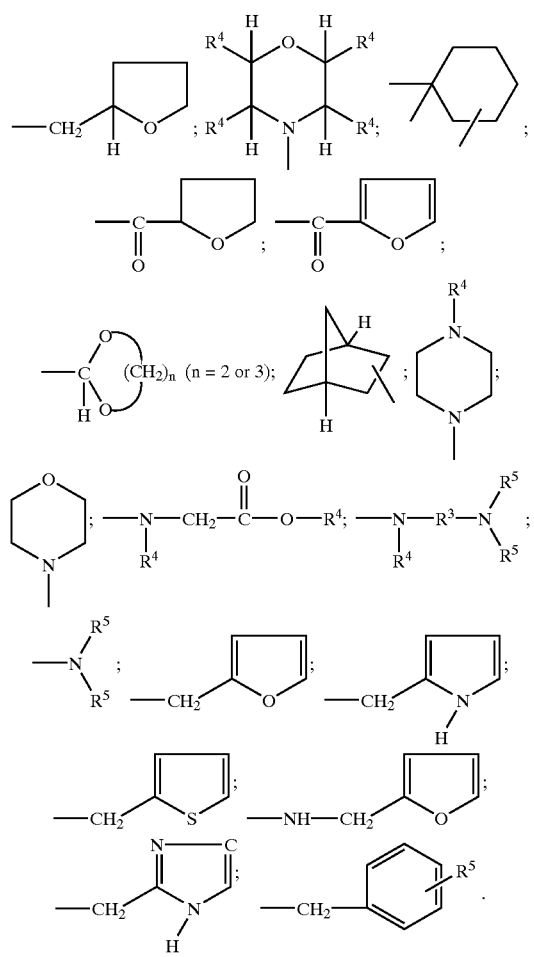

These formulae are illustrative and not restrictive.

Preference is given to groups in which the readily abstractable H atoms are H atoms in the α-position to a double bond (allylic H atoms). RGb are particularly preferably

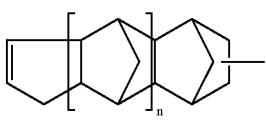

RGb1 n = 0–10 groups.

Methods for the incorporation of such structures are, for example, the concomitant use of the esters of (oligo) dihydrodicyclopentadienol.

The maleate/fumarate monoesters of (oligo) dihydrodicyclopentadienol are readily available industrially from maleic acid and DCPD.

These monoesters are obtainable in a smooth reaction from maleic anhydride (MA), water and dicyclopentadiene (DCPD) or by a direct addition reaction of DCPD with MA. It is furthermore possible to add DCPD directly onto other acids and/or acidic polyesters. However, these reactions usually proceed worse and require catalysis, for example by $BF_3$ etherate.

It is furthermore known, for example from U.S. Pat. No. 252,682, that side-reactions as shown in the following equation can occur to a minor extent in the reaction of DCPD and MA. These by-products likewise serve to introduce structures of the general formula RGb1.

Furthermore, dihydrodicyclopentadienol and dihydrodicyclopentadienol acrylate are commercially available and are suitable for introduction of the particularly preferred RGb structures.

Hydroxyl-functional compounds for introduction of groups of the general formula RGb1 are dihydrodicyclopentadienyl alcohol and preferably the inexpensive adducts of DCPD with glycols which can be obtained with acid catalysis, in accordance with the following equation:

Also of interest as RGb are endomethylenetetrahydrophthalic acid structures, which are generally accessible, for example, by adduction of CPD onto the maleate groups.

Of particular interest is the introduction of endomethylenetetrahydrophthalic acid structures by adduction of CPD onto the double bonds of unsaturated polyesters.

Also of interest, is the introduction of endomethylenetetrahydrophthalic acid and tetrahydrophthaoic acid structures via the imides of these acids with hydroxyalkylamines, as disclosed, for example, in DE-A-15700273 or DE-A-17200323.

The oligomeric and/or polymeric basic structure of the polymer IIa covers the known polymers, as built up, for example, by —C—C— linkages, which may also have double and/or triple bonds, and by ether, ester, urethane, amide, imide, imidazole, ketone, sulfide, sulfone, acetal, urea, carbonate and siloxane linkages, with the proviso of the functionalization defined in greater detail above.

Preference is given to polyesters, polyethers, polyurethanes and particularly preferably polyacrylates.

For the purposes of the present invention, polyesters are saturated and unsaturated polyester resins.

For building up the polyester resins, the conventional and known carboxylic acids having $\geq 2$ carboxyl groups and/or their anhydrides and/or their esters and hydroxyl compounds having $\geq 2$ OH groups are suitable. It is also possible to use in addition monofunctional compounds in order, for example, to regulate the molecular weight of the polycondensates.

Examples of suitable carboxylic acid components are $\alpha,\beta$-ethylenically unsaturated carboxylic acids, such as maleic acid, maleic anhydride, fumaric acid, itaconic acid, citraconic acid, saturated aliphatic carboxylic acids or their anhydrides, such as succinic acid, adipic acid, suberic acid, sebacic acid, azelaic acid, natural fatty acids and polymerized natural fatty acids, such as linoleic acid, dimeric and polymeric linseed oil fatty acid, castor oil, castor oil fatty acid, saturated cycloaliphatic carboxylic acids and their anhydrides, such as tetrahydrophthalic acid, hexahydrophthalic acid, endomethylenetetrahydrophthalic acid, norbornenedicarboxylic acid, aromatic carboxylic acids and their anhydrides, such as phthalic acid in its isomeric forms, also tri- and tetracarboxylic acids and their anhydrides, such as trimellitic acid, pyromellitic acid, polycarboxylic acids which have been partially esterified by means of allyl alcohol, for example monoallyl trimellitate or diallyl pyromellitate, where benzophenonecarboxylic acids are of particular importance since structures which can be excited by means of UV light can be incorporated via these copolymers.

Examples of suitable hydroxyl components are optionally alkoxylated, at least dihydric aliphatic and/or cycloaliphatic alcohols, such as ethylene glycol, propylene glycol, polyethylene glycols, polypropylene glycols, butanediol oligomers, hexanediol, trimethylolpropane, pentaerythritol, neopentyl glycol, cyclohexanedimethanol, bisphenol A, hydrogenated bisphenol A, OH-polyfunctional polymers, such as hydroxyl-modified polybutadienes or hydroxyl-carrying polyurethane prepolymers, glycerol, mono- and diglycerides of saturated and unsaturated fatty acids, in particular monoglycerides of linseed oil or sunflower oil. Also suitable are unsaturated alcohols, such as polyfunctional hydroxyl compounds which have been (partially) etherified by means of allyl alcohol, for example trimethylolethane monoallyl ether, trimethylolethane diallyl ether, trimethylolpropane monoallyl ether, trimethylolpropane diallyl ether, pentaerythritol monoallyl ether, pentaerythritol diallyl ether, 2-butene-1,4-diol and alkoxylated 2-butene-1, 4-diol.

If monofunctional substances are employed for regulation of the molecular weight, these are preferably monofunctional alcohols such as ethanol, propanol, butanol, hexanol, decanol, isodecanol, cyclohexanol, benzyl alcohol or allyl alcohol. For the purposes of the present invention, the term polyester also includes polycondensates containing amide and/or imide groups in addition to the ester groups, as obtained by concomitant use of amino compounds. Polyesters modified in this way are disclosed, for example, in DE-A-15700273 and DE-A-17200323. If endomethylenetetrahydrophthalic acid and tetrahydrophthalic acid structures are introduced via the imides of these acids with hydroxylamines, as mentioned therein, the RGb is in accordance with this invention.

DCPD can also be adducted onto the double bonds of the unsaturated polyesters used, enabling incorporation of endomethylenetetrahydrophthalic acid structures which represent the RGb for the purposes of this invention. These endomethylenetetrahydrophthalic acid structures may be present on the polyester double bonds on the chain and/or on terminal double bonds, as introduced, for example, via substances of the general formula 3. Double bonds from the unsaturated dicarboxylic acids and/or unsaturated diols are RGb on the chain for the purposes of the invention. Introduction of the RG can take place by cocondensation and/or by polymer-analogous reactions with polyesters containing functional groups. Examples of cocondensations are the concomitant use of trimethylolpropane diallyl and monoallyl ethers, pentaerythritol diallyl and monoallyl ethers, 2-butene-1,4-diol, alkoxylated 2-butene-1,4-diol, allyl alcohol and compounds of the formulae 3, 4, 5, 7 and 8.

RGa is preferably introduced by cocondensation of benzophenonecarboxylic acids or their anhydrides. Further preference is given to the addition reaction of the products of the reaction of hydroxybenzophenones with an excess of diisocyanates containing hydroxyl-functional polyesters.

In this way, RGb can also be introduced into hydroxyl-functional polyesters. To this end, diisocyanates containing isocyanate groups of different reactivity, for example isophorone diisocyanate or 1,4-tolylene diisocyanate, are initially preferably reacted with a semi-equivalent amount of, for example, hydroxyacrylates, hydroxyvinyl ethers, hydroxyallyl esters, hydroxyallyl ethers, hydroxy-DCPD compounds of the formulae AGb4 and AGb6, and these reaction products are then reacted with the hydroxyl-functional polyesters. In said reactions, hydroxyl-functional substances of different types can also be employed at the same time.

Poly(meth)acrylate resins which have been functionalized in accordance with the invention with RG represent a further important polymer class according to the invention and are obtained by copolymerization of acrylates, if desired with further copolymerizable, compounds.

However, the poly(meth)acrylate resins according to the invention can also be prepared in solvents. A further advantageous method for the preparation of poly(meth)acrylates is solvent-free, free-radical bulk polymerization in a stirred reactor, if desired under pressure or in continuous reactors at temperatures above the melting point of the polymers formed.

Suitable components for building up poly(meth)acrylate resins are, for example, the known esters of acrylic acid and methacrylic acid with aliphatic, cycloaliphatic, araliphatic and aromatic alcohols having 1 to 40 carbon atoms, for example methyl (meth)acrylate, ethyl (meth)acrylate, propyl (meth)acrylate, isopropyl (meth)acrylate , n-butyl (meth)acrylate, isobutyl (meth)acrylate, tert-butyl (meth)acrylate, amyl (meth)acrylate, isoamyl (meth)acrylate, hexyl (meth) acrylate, 2-ethylhexyl (meth)acrylate, decyl (meth)acrylate, undecyl (meth)acrylate, dodecyl (meth)acrylate, tridecyl (meth)acrylate, cyclohexyl (meth)acrylate, methylcyclohexyl (meth)acrylate, benzyl (meth)acrylate, tetrahydrofurfuryl (meth)acrylate, fufuryl (meth)acrylate and the esters of 3-phenylacrylic acid and their various isomeric forms, such as methyl cinnamate, ethyl cinnamate, butyl cinnamate, benzyl cinnamate, cyclohexyl cinnamate, isoamyl cinnamate, tetrahydrofurfuryl cinnamate, furfuryl cinnamate, acrylamide, methacrylamide, methylolacrylamide, methylolmethacrylamide, acrylic acid, methacrylic acid, 3-phenylacrylic acid, hydroxyalkyl (meth) acrylates, such as ethyl glycol mono(meth)acrylate, butyl glycol mono(meth)acrylate, hexanediol mono(meth) acrylate, glycol ether (meth)acrylates, such as methoxyethyl glycol mono(meth)acrylate, ethoxyethyl glycol mono(meth) acrylate, butoxyethyl glycol mono(meth)acrylate, phenoxyethyl glycol mono(meth)acrylate, glycidyl acrylate, glycidyl methacrylate, amino(meth)acrylates, such as 2-aminoethyl (meth)acrylate.

Suitable further components are free-radical-copolymerizable monomers, such as styrene, 1-methylstyrene, 4-tert-butylstyrene, 2-chlorostyrene, vinyl esters of fatty acids having 2 to 20 carbon atoms, such as vinyl acetate, vinyl propionate, vinyl ethers of alkanols having 2 to 20 carbon atoms, such as vinyl isobutyl ether, vinyl chloride, vinylidene chloride, vinyl alkyl ketones, dienes, such as butadiene and isoprene, and esters of maleic and crotonic acid. Other suitable monomers are cyclic vinyl compounds, such as vinylpyridine, 2-methyl-1-vinylimidazole, 1-vinylimidazole, 5-vinylpyrrolidone and N-vinylpyrrolidone. It is also possible to use allylic unsaturated monomers, for example allyl alcohol, allylalkyl esters, monoalkyl phthalate and allyl phthalate. Acrolein and methacrolein and polymerizable isocyanates are also suitable.

The incorporation of RG can take place by copolymerization during preparation of the polyacrylates or by subsequent polymer-analogous reaction. Readily polymerizable compounds containing RGb groups are, for example, dihydrodicyclopentadienyl (meth)acrylate, dihydrodicyclopentadienyl ethacrylate and dihydrodicyclopentadienyl cinnamate. Readily polymerizable compounds containing further groups at which polymer-analogous functionalization is possible are, for example, copolymerizable epoxide compounds, such as glycidyl (meth)acrylate or hydroxyalkyl (meth)acrylates. The hydroxyl and/or epoxide groups incorporated in this way are anchor groups for polymer-analogous functionalization reactions of the polymers. Epoxide groups are suitable, for example, for the introduction of acrylic double bonds by reaction with (meth)acrylic aced (RGb) and/or for introduction of vinyl ether groups (RGb) by reaction with aminovinyl ether compounds, for example diethanolaminedivinyl ether, or for introduction of benzophenone groups (RGa) by reaction with hydroxy- and/or aminobelzophenones.

Polyurethanes which have been functionalized according to the invention by means of RG represent a further important polymer class according to the invention and are obtained by the manner known to the person skilled in the art from polyfunctional, usually difunctional isocyanates and polyhydroxyl and/or polyamino compounds. Here too, it is possible for RGa and/or RGb to be incorporated directly during build-up of the polyurethanes or to be introduced subsequently into functional polyurethanes. The chemical reactants here are essentially the same as in the polymers described above. RGa are preferably introduced by concomitant use of functional benzophenone compounds and RGb via hydroxy-DCPD compounds of the formulae RGb4 and RGb6.

Further details regarding the parent polyurethane structures which can be used are given in the corresponding discussion of the polyurethanes which can be used as polymer IIb.

The polymer IIa according to the invention is prepared by generally known rules and is known to the person skilled in the art of polymers, which relates, for example, to the establishment of a desired molecular weight by concomitant use of regulating or monofunctional starting materials or setting of a desired glass transition temperature by balancing hard/soft components.

Compounds which are particularly suitable for introduction of RGa into polymers IIa used in accordance with the invention, in particular into epoxide- and/or hydroxyl-functionalized polyesters, polyurethanes or polyacrylates as described above, are the following:

2-, 3- and 4-hydroxybenzophenone, 2-hydroxy-5-methylhydroxybenzophenone, 2-hydroxy-4-methoxybenzophenone, 2-hydroxy-4-octyloxybenzophenone, 2-hydroxy-4-dodedyloxybenzophenone, 2-hydroxy-5-chlorohydroxybenzophenone, 2-hydroxy-4-methoxy-4'-methylbenzophenone, 2-hydroxy-4-methoxy-4'-chlorobenzophenone, 4-hydroxy-3-methylbenzophenone, 4-hydroxy-4'-methoxybenzophenone, 4-hydroxy-4'- chlorobenzophenone, 4-hydroxy-4'-fluorobenzophenone, 4-hydroxy-4'-cyanobenzophenone, 4-hydroxy-2',4'-dimethoxybenzophenone, 2,2',4,4'- and 2,4-dihydroxybenzophenone, 4-tert-butyl-2,4-dihydroxybenzophenone, 2,2'-dihydroxy-4-methoxybenzophenone, 2,2'-dihydroxy-4-octoxybenzophenone, 2,2'-dihydroxy-4,4'-dimethoxybenzophenone, 2,4,4'-, 2,3,4- and 2,4,6-trihydroxybenzophenone, 2,2'-, 4,4'-, 2,3,4,4'- and 2,3',4,4'-tetrahydroxybenzophenone, 2-, 3- and 4-aminobenzophenone, 2-amino-4-methylbenzophenone, 2-amino-6-methylbenzophenone, 2-amino-4'-methylbenzophenone, 2-amino-4'-chloro-5-fluorobenzophenone, 2-amino-5-chlorobenzophenone, 2-amino-5-bromobenzophenone, 2-amino-5-methylbenzophenone, 2-amino-N-ethylbenzophenone, 2-amino-2',5'-dimethylbenzophenone, 4-amino-2-chlorobenzophenone, 4-amino-4'-methyoxybenzophenone, 3,4-, 4,4'- and 3,3'-diaminobenzophenone, 4,4'-bis(methylamino)benzophenone, 3,3',4,4'-tetraaminobenzophenone, 2-, 3- and 4-benzoylbenzoic acid, 2-benzoyl-3'-methylbenzoic acid, 2-benzoyl-4'-ethylbenzoic acid, 2-benzoyl-3,6-dimethylbenzoic acid, 2-benzoyl-2',6'-dimethylbenzoic acid, 2-benzoyl-3',4'-dimethylbenzoic acid, 2-benzoyl-2',4',6-dimethylbenzoic acid, 2-benzoyl-p-hydroxybenzoic acid, 2-benzoyl-4'-methyl-3'-chlorobenzoic acid, 2-benzoyl-6-chlorobenzoic acid, 4-benzoyl-4'-isopropylbenzoic acid, 4-benzoyl-4'-chlorobenzoic acid, 4-benzoyl-4'-(2-carboxypropyl)benzoic acid, 2,4-, 3,4- and 4,4'-benzophenonedicarboxylic acid, 2',3,4-, 3,3',4- and 3,4,4'-benzophenonetricarboxylic acid, 3,3',4,4'-benzophenonetetracarboxylic acid and -tetracarboxylic acid dianhydride, 2-hydroxy-4-methoxy-5-sulfobenzophenone, 4-(4-carboxyphenoxy)benzophenone, 4-(3,4-bis(carboxy)phenoxy)benzophenone and the corresponding anhydride, 4'-(4-carboxyphenoxy)benzophenone-4-carboxylic acid, 4'-(4-carboxyphenoxy)benzophenone-3,4-dicarboxylic acid and the corresponding anhydride, 4'-(3,4-bis(carboxy)phenoxy)benzophenone-2,4- and -3,4-dicarboxylic acid and the corresponding anhydrides, 4-(4-cyanobenzoyl)thiophenol, 4-(2-hydroxyethoxy)phenyl-(2-hydroxy-2-propyl) ketone, 4-(2-aminoethoxy)phenyl-(2-hydroxy-2-propyl) ketone, 4-(2-hydroxycarbonylmethoxy)phenyl-(2-hydroxy-2-propyl) ketone, 4-(2-isocyanatoethoxy)phenyl 2-hydroxy-2-propyl ketone, 4-(2-isocyanoatomethoxy) phenyl 2-hydroxy-2-propyl ketone, 2-([2-(6-isocyanatohexylaminocarbonyloxy)ethoxythioxanthone and phenylglyoxylic acid.

Furthermore, the polymers and copolymers discussed below under "polymers IIb" can also be used as polymers IIa so long as they are provided with reactive groups RG, in particular RGa and/or RGb. Polymers and copolymers provided with reactive groups RG which may be mentioned particularly here are halogen-containing olefinic compounds (group 4f).

The crosslinking of the polymers IIa used in accordance with the invention is preferably carried out by high-energy radiation, in particular by UV light. In most cases, further addition of photoinitiator is not necessary, ie. the substances are self-photocrosslinking, a particular advantage being their low inhibition by air. However, it is not excluded to add further commercially available photoinitiators. Furthermore, many polymers IIa are also thermally crosslinkable. Particularly high thermal crosslinkability is achieved in the presence of peroxides and/or C—C-labile substances of the benzopinacole type in unsaturated systems which additionally contain DCPD groups. Such systems are in some cases thermally curable even without peroxides. Rapid crosslinking, which is preferred, is achieved by combined use of heat and UV light, for example by a combination of IR and UV sources.

The polymers IIb are thermoplastic and ion-conducting polymers. Particular mention should be made of the following:

1) Homopolymers, block polymers or copolymers (polymers IIb1) obtainable by polymerization of
   b1) from 5 to 100% by weight, based on the polymers IIb1, of a condensation product of
      a) at least compound (a) which is capable of reacting with a carboxylic acid or a sulfonic acid or a derivative or a mixture of two or more thereof, and
      b) at least 1 mol, per mole of this compound (a), of a carboxylic acid or sulfonic acid (b) containing at least one free-radical-polymerizable functional group, or a derivative thereof or a mixture of two or more thereof, and
   b2) from 0 to 95% by weight, based on the polymer IIb1, of a further compound (c) having a mean molecular weight (number average) of at least 5000 containing polyether segments in the main or side chain.

The polymer IIb1 is preferably obtainable by polymerization of
   b1) from 5 to 100% by weight, based on the polymer IIb1, of a condensation product of
      a polyhydric alcohol containing carbon and oxygen atoms in the main chain, and
      b) at least 1 mol, per mole of the polyhydric alcohol, of an α,β-unsaturated carboxylic acid, and
   b2) from 0 to 95% by weight, based on the polymer IIb1, of a further compound (c) having a mean molecular weight (number average) of at least 5000 containing polyether segments in the main or side chain.

The compound (a) which is capable of reacting with a carboxylic acid or a sulfonic acid (b) or a derivative or mixture of two or more thereof can in principle be any compound which satisfies this criterion and contains no reactive groups RG.

The compound (a) is preferably selected from group consisting of monohydric and polyhydric alcohols containing exclusively carbon atoms in the main chain; monohydric and polyhydric alcohols containing at least one atom selected from the group consisting of oxygen, phosphorus and nitrogen in the main chain in addition to at least two carbon atoms; silicon-containing compounds; amines containing at least one primary amino group; amines containing at least one secondary amino group; aminoalcohols; thiols containing one or more thiol groups; compounds containing at least one thiol group and at least one hydroxyl group; and a mixture of two or more thereof.

Of these preference is in turn given to compounds (a) containing two or more functional groups which are capable of reacting with carboxylic acids or sulfonic acids.

If use is made of compounds (a) containing amino groups as functional group, it is preferred to use those containing secondary amino groups, so that; after the condensation, either no free NH groups, or only a small amount of free NH groups, are present in the composition.

Preferred compounds (a) which may be mentioned in detail are the following:
   monohydric and polyhydric alcohols containing exclusively carbon atoms in the main chain, having 1 to 20, preferably 2 to 20, in particular 2 to 10, alcholic OH groups, in particular dihydric, trihydric and tetrahydric alcohols, preferably having 2 to 20 carbon atoms, for example ethylene glycol, 1,2- and 1,3-propanediol, 1,2- and 1,3-butanediol, 1,4-butenediol, 1,4-butynediol, 1,6-hexanediol, neopentyl glycol, 1,2-dodecanediol, glycerol, trimethylolpropane, pentaerythritol and sugar alcohols, hydroquinone, novolak, bisphenol A, but it is also possible, as evident from the above definition, to employ monohydric alcohols, for example methanol, ethanol, propanol, n-, sec- or tert-butanol; it is furthermore also possible to use polyhydroxyolefins, preferably those having two terminal hydroxyl groups, for example α,ω-dihydroxybutadiene; polyester polyols, as disclosed, for example, in Ullmann's *Encyklopädie der technischen Chemie* [Ullmann's Encyclopedia of Industrial Chemistry], 4$^{th}$ Edition, Vol. 19, pp. 62–65, which are obtained, for example, by reacting dihydric alcohols with polybasic, preferably dibasic polycarboxylic acids; monohydric and polyhydric alcohols containing at least one oxygen atom in the main chain, in addition to at least two carbon atoms, preferably polyether alcohols, for example products of the polymerization of alkylene epoxides preferably isobutylene oxide, propylene oxide, ethylene oxide, 1,2-epoxybutane, 1,2-epoxypentane, 1,2-epoxyhexane, tetrahydrofuran, styrene oxide, where polyether alcohols modified at the terminal groups, for example polyether alcohols modified by means of $NH_2$ terminal groups, can also be used; these alcohols preferably have a molecular weight (number average) of from 100 to 5000, further preferably from 200 to 1000, in particular from 300 to 800; such compounds are known per se and are commercially available under the tradenames Pluriol® Pluronic® (BASF Aktiengesellschaft);

alcohols as defined above in which some or all of the carbon atoms have been replaced by silicon, where in particular polysiloxanes or alkylene oxide-siloxane copolymers or mixtures of polyether alcohols and polysiloxanes, as described, for example, in EP-B 581 296 and EP-A 525 728, can be used here, the comments made above regarding the molecular weight these alcohols likewise applying here;

alcohols as defined above, in particular polyether alcohols, in which some or all of the oxygen atoms have been replaced by sulfur atoms, the comments made above regarding the molecular weight of these alcohols likewise applying here;

monohydric and polyhydric alcohols containing at least one phosphorus atom or at least one nitrogen atoms in the main chain in addition to at least two carbon atoms, for example diethanolamine, triethanolamine;

lactones derived from compounds of the general formula HO—$(CH_2)_z$—COOH, where z is a number from 1 to 20, for example ε-caprolactone, β-propiolaetone, γ-butyrolactone or methyl-ε-caprolactone;

silicon-containing compounds, for example di- and trichlorosilane, phenyltrichlorosilane, diphenyldichlorosilane, dimethylvinylchlorosilane; silanols, for example trimethylsilanol;

amines containing at least one primary and/or secondary amino group, for example butylamine, 2-ethylhexylamine, ethylenediamine, hexamethylenediamine, diethylenetriamine, tetraethylenepentamine, pentaethylenehexamine, aniline and phenylenediamine;

polyetherdiamines, for example 4,7-dioxydecane-1,10-diamine, 4,11-dioxytetradecane-1,14-diamine;

thiols containing one or more thiol groups, for example aliphatic thiols, for example methanethiol, ethanethiol, cyclohexanethiol and dodecanethiol; aromatic thiols, for example thiophenol, 4-chlorothiophenol and 2-mercaptoaniline;

compounds containing at least one thiol group and at least one hydroxyl group, for example 4-hydroxythiophenol and monothio derivatives of the polyhydric alcohols defined above;

aminoalcohols, for example ethanolamine, N-methylethanolamine, N-ethylethanolamine, N-butylethanolamine, 2-amino-1-propanol and 2-amino-1-phenylethanol;

mono- and polyaminopolyols containing more than two aliphatically bound hydroxyl groups, for example tris(hydroxymethyl)methylamine, glucamine and N,N'-bis(2-hydroxyethyl)ethylenediamine, and mixtures thereof.

It is also possible to employ mixtures of two or more of the compounds (a) described above.

The abovementioned compounds (a) are condensed according to the invention with a carboxylic acid or sulfonic acid (b) containing at least one free-radial-polymerizable functional group, or a derivative thereof or a mixture of two or more thereof, where at least one, preferably all, of the free groups, within the compounds (a), which are capable of condensation are condensed with the compound (b).

For the purposes of the present invention, the carboxylic acid or sulfonic acid (b) can in principle be any carboxylic or sulfonic acid containing at least one free-radical-polymerizable functional group, and derivatives thereof. The term "derivatives" used here covers both compounds derived from a carboxylic or sulfonic acid which has been modified at the acid function, for example esters, acid halides and acid anhydrides, and compounds derived from a carboxylic or sulfonic acid which has been modified on the carbon skeleton of the carboxylic or sulfonic acid, for example halocarboxylic or halosulfonic acids.

The following may be mentioned in particular as compound (b):

α,β-unsaturated carboxylic acids or β,γ-unsaturated carboxylic acids or derivatives thereof.

Particularly suitable α,β-unsaturated carboxylic acids are those of the formula:

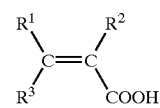

in which $R^1$, $R^2$ and $R^3$ are hydrogen or $C_1$- to $C_4$-alkyl radicals, where of these acrylic acid and methacrylic acid are in turn preferred;

also highly suitable are cinnamic acid, maleic acid, fumaric acid, itaconic acid and p-vinylbenzoic acid, and derivatives thereof, for example anhydrides, for example maleic anhydride and itaconic anhydride;

halides, in particular chlorides, for example acryloyl and methacryloyl chloride; esters, for example (cyclo)alkyl (meth)acrylates having up to 20 carbon atoms in the alkyl radical, for example methyl, ethyl, propyl, butyl, hexyl, 2ethylhexyl, stearyl, lauryl, cyclohexyl, benzyl, trifluoromethyl, hexafluotopropyl, and tetrafluoropropyl (meth)acrylate, polypropylene glycol mono(meth)acrylates, polyethylene mono(meth)acrylates, poly(meth)acrylates of polyhydric alcohols, for example glycerol di(meth)acrylate, trimethylolpropane di(meth)acrylate, pentaerythritol di- or tri(meth)acrylate, diethylene glycol bis(mono-(2-acryloxy)ethyl)carbonate, poly(meth)acrylates of alcohols which themselves in turn contain a free-radical-polymerizable group, for example esters of (meth)acrylic acid and vinyl and/or allyl alcohol;

vinyl esters of other aliphatic or aromatic carboxylic acids, for example vinyl acetate, vinyl propionate, vinyl butanoate, vinyl hexanoate, vinyl octanoate, vinyl decanoate, vinyl stearate, vinyl palmitate, vinyl crotonate, divinyl adipate, divinyl sebacate, vinyl 2-ethylhexanoate, vinyl trifluoroacetate; allyl esters of other aliphatic or aromatic carboxylic acids, for example allyl acetate, allyl propionate, allyl butanoate, allyl hexanoate, allyl octanoate, allyl decanoate, allyl stearate, allyl palmitate, allyl crotonate, allyl salicylate, allyl lactate, diallyl oxalate, allyl succinate, diallyl glutarate, diallyl adipate, diallyl pimelate, diallyl cinnamate, diallyl maleate, diallyl phthalate, diallyl isophthalate, triallyl benzene-1,3,5-tricarboxylate, allyl fluoroacetate, allyl perfluorobutyrate, allyl perfluorooctanoate;

$\beta,\gamma$-unsaturated carboxylic acids and their derivatives, for example vinylacetic acid, 2-methylvinylacetic acid, isobutyl 3-butenoate, allyl 3-butenoate, allyl 2-hydroxy-3-butenoate and diketene;

sulfonic acids, for example vinylsulfonic acid, allyl- and methallylsulfonic acid, and esters and halides thereof, vinyl benzenesulfonate and 4-vinylbenzenesulfonamide.

It is also possible to employ mixtures of two or more of the carboxylic and/or sulfonic acids described above.

The polymer IIb1 can be obtained by reacting from 5 to 100% by weight, preferably from 30 to 70% by weight, based on the polymer IIb1, of the condensation product defined above and from 0 to 95% by weight, in particular from 30 to 70% by weight, based on the polymer IIb1, of a compound (c).

2) Homopolymers, block polymers or copolymers IIb2 (polymers IIb2) obtainable by polymerization of b1) from 5 to 75% by weight, based on the polymer IIb2, of a compound (d)which is capable of polymerization, preferably of an unsaturated compound (d) which is capable of free-radical polymerization and which is different from the above carboxylic acid or sulfonic acid or a derivative thereof or a mixture of two or more thereof and b2) from 25 to 95% by weight, based on the polymer IIb2, of the further compound (c) having a mean molecular weight (number average) of at least 5000 containing polyether segments in the main or side chain.

The following may be mentioned specifically as compound (d) which can be used for the preparation of the polymer IIb2 and is capable of free-radical polymerization:

olefinic hydrocarbons, for example ethylene, propylene, butylene, isobutylene, hexene or higher homologs and vinylcyclohexane; (meth)acrylonitrile;

halogen-containing olefinic compounds, for example vinylidene fluoride, vinylidene chloride, vinyl fluoride, vinyl chloride, hexafluoropropene, trifluoropropene, 1,2-dichloroethylene, 1,2-difluoroethylene and tetrafluoroethylene;

vinyl alcohol, vinyl acetate, N-vinylpyrrolidone, N-vinylimidazole and vinylformamide;

phosphorus nitride chlorides, for example phosphorus dichloride nitride, hexachloro(triphosphazenes) and derivatives thereof which are partially or fully substituted by alkoxy, phenoxy, amino and fluoroalkoxy groups, ie. compounds which can be polymerized to give polyphosphazenes;

aromatic olefinic compounds, for example styrene, $\alpha$-methylstyrene;

vinyl ethers, for example methyl, ethyl, propyl, isopropyl, butyl, isobutyl, hexyl, octyl, decyl, dodecyl, 2-ethylhexyl, cyclohexyl, benzyl, trifluoromethyl, hexafluoropropyl and tetrafluoropropyl vinyl ether.

It is, of course, also possible to employ mixtures of the above compounds (d), in which case copolymers are formed which, depending on the preparation method, contain the monomers in a random distribution, or block copolymers result.

These compounds (d), like the condensation products described above, are polymerized in a conventional manner known to the person skilled in the art, preferably by free-radical polymerization, where the comments made above regarding the compound (c) regarding the molecular weights obtained also apply here.

Suitable compounds (c) are primarily compounds having a mean molecular weight (number average) of at least 5000, preferably from 5000 to 20,000,000, in particular from 100,000 to 6,000,000 which are capable of solvating lithium cations and functioning as binders.

Suitable compounds (c) are, for example, polyethers and copolymers containing at least 30% by weight of the following structural unit, based on the total weight of the compound (c):

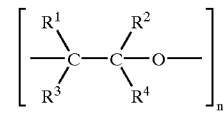

where $R^1$, $R^2$, $R^3$ and $R^4$ are aryl groups, alkyl groups, preferably methyl groups, or hydrogen, are identical or different and may contain heteroatoms, such as oxygen, nitrogen, sulfur or silicon.

Such compounds are described, for example, in: M. B. Armand et al., Fast Ion Transport in Solids, Elsevier, New York, 1979, pp. 131–136, or in FR-A 7832976.

The compound (c) can also consist of mixtures of such compounds.

The polymer IIb2 can be obtained by reacting from 5 to 75% by weight, preferably from 30 to 70% by weight, based on the polymer IIb2, of a compound (d) and from 25 to 95% by weight, in particular from 30 to 70% by weight, based on the polymer IIb2, of a compound (c).

3) Polycarbonates, for polyethylene carbonate, polypropylene carbonate, polybutadiene carbonate or polyvinylidene carbonate.

4) Homopolymers, block polymers and copolymers a) to g), ie. those prepared from a) olefinic hydrocarbons, for example ethylene, propylene, butylene, isobutene, propene, hexene or higher homologs, butadiene, cyclopentene, cyclohexene, norbornene, vinylcyclohexane, 1,3-pantadiene, 1,3-, 1,4- or 1,5-hexadiene, isoprene or vinylnorbornene;

b) aromatic hydrocarbons, for example styrene or methylstyrene;

c) acrylates or methacrylates, such as methyl, ethyl, propyl, isopropyl, butyl, isobutyl, hexyl, octyl, decyl, dodecyl, 2-ethylhexyl, cyclohexyl, benzyl, trifluoromethyl, hexafluoropropyl or tetrafluoropropyl acrylate or methacrylate;

d) acrylonitrile, methacrylonitrile, N-methylpyrrolidone, N-vinylimidazole or vinyl acetate;

e) vinyl ethers, for example methyl, ethyl, propyl, isopropyl, butyl, isobutyl, hexyl, octyl, decyl, dodecyl, 2-ethylhexyl, cyclohexyl, benzyl, trifluoromethyl, hexafluoropropyl or tetrafluoropropyl vinyl ether; and f) Polymers and copolymers of halogen-containing olefinic compounds, for example vinylidene fluoride, vinylidene chloride, vinyl fluoride, vinyl chloride, hexafluoropropene, trifluoropropene, 1,2-dichloroethylene, 1,2-difluoroethylene and tetrafluoroethylene; preferably polymers or copolymers of vinyl chloride, acrylonitrile or vinylidene fluoride; copolymers of vinyl chloride and vinylidene chloride, vinyl chloride and acrylonitrile, vinylidene fluoride and hexafluoropropylene, vinylidene fluoride with hexafluoropropylene; terpolymers of vinylidene fluoride and hexafluoropropylene and a member of the group consisting of vinyl fluoride, tetrafluoroethylene and a trifluoroethylene; in particular a copolymer of vinylidene fluoride and hexafluoropropylene; and further preferably copolymer comprising from 75 to 92% by weight of vinylidene fluoride and from 8 to 25% by weight of hexafluoropropylene.

g) 2-vinylpyridine, 4-vinylpyridine or vinylene carbonate.

In the preparation of the abovementioned polymers, regulators, for example mercaptans, can be employed if necessary and/or desired.

5) Polyurethanes, for example obtainable by reacting a) organic diisocyanates having 6 to 30 carbon atoms, for example aliphatic, non-cyclic diisocyanates, for example 1,5-hexamethylene diisocyanate and 1,6-hexamethylene diisocyanate, aliphatic cyclic diisocyanates, for example 1,4-cyclohexylene diisocyanate, dicyclohexylmethane diisocyanate and isophorone diisocyanate, or aromatic diisocyanates, for example tolylene 2,4-diisocyanate, tolylene 2,6-diisocyanate, m-tetramethylxylene diisocyanate, p-tetramethylxylene diisocyanate, 1,5-tetrahydronaphthylene diisocyanate and 4,4'-diphenylmethane diisocyanate, or mixtures of these compounds, with b) polyhydric alcohols, for example polyesterols, polyetherols and diols.

The polyesterols are advantageously predominantly linear polymers containing terminal OH groups, preferably those containing two or three, in particular two, terminal OH groups. The acid number of the polyesterols is less than 10, preferably less than 3. The polyesterols can be prepared in a simple manner by esterification of aliphatic or aromatic dicarboxylic acids having 4 to 15 carbon atoms, preferably 4 to 6 carbon atoms, using glycols, preferably glycols having 2 to 25 carbon atoms, or by polymerization of lactones having 3 to 20 carbon atoms. Examples of dicarboxylic acids which can be employed are glutaric acid, pimelic acid, suberic acid, sebacic acid, dodecanoic acid and preferably adipic acid and succinic acid. Suitable aromatic dicarboxylic acids are terephthalic acid, isophthalic acid, phthalic acid or mixtures of these dicarboxylic acids with other dicarboxylic acids, for example diphenic acid, sebacic acid, succinic acid and adipic acid. The dicarboxylic acids can be used individually or as mixtures. For the preparation of the polyesterols, it may be advantageous to replace the dicarboxylic acids by the corresponding acid derivatives, such as carboxylic anhydrides or carbonyl chlorides. Examples of suitable glycols are diethylene glycol, 1,5-pentanediol, 1,10-decanediol and 2,2,4-trimethyl-1,5-pentanediol. Preference is given to 1,2-ethanediol, 1,3-propanediol, 2-methyl-1,3-propanediol, 1,4-butanediol, 1,6-hexanediol, 2,2-dimethyl-1,3-propanendiol, 1,4-dimethylolcyclohexane, 1,4-diethanolcyclohexane and ethoxylated or propoxylated products of 2,2-bis(4-hydroxyphenylene)propane (bisphenol A). Depending on the desired properties of the polyurethanes, the polyols can be used alone or as a mixture in various mixing ratios. Suitable lactones for the preparation of polyesterols are, for example α,α-dimethyl-β-propiolactone, γ-butyrolactone and preferably ε-caprolactone.

The polyetherols are essentially linear substances containing terminal hydroxyl groups and containing ether bonds. Suitable polyetherols can easily be prepared by polymerization of cyclic ethers, such as tetrahydrofuran, or by reaction of one or more alkylene oxides having 2 to 4 carbon atoms in the alkylene radical with an initiator molecule containing two active hydrogen atoms bonded in the alkylene radical. Examples of suitable alkylene oxides are ethylene oxide, 1,2-propylene oxide, epichlorohydrin, 1,2-butylene oxide and 2,3-butylene oxide. The alkylene oxides can be used individually, alternately one after the other or as a mixture. Examples of suitable initiator molecules are water, glycols, such as ethylene glycol, propylene glycol, 1,4-butanediol and 1,6-hexanediol, amines, such as ethylenediamine, hexamethylenediamine and 4,4'-diaminodiphenylmethane, and aminoalcohols, such as ethanolamine. Suitable polyesterols and polyetherols and their preparation are described, for example, in EP-B 416 386, and suitable polycarbonate diols, preferably those based on 1,6-hexanediol, and their preparation are described, for example in U.S. Pat. No. 4,131,731.

In amounts of up to 30% by weight, based on the total weight of the alcohols; aliphatic diols having 2 to 20, preferably 2 to 10, carbon atoms, such as 1,2-ethanediol, 1,3-propanediol, 1,4-butanediol, 1,6- hexanediol, 1,5-pentanediol, 1,10-decanediol, 2-methyl-1,3-propanediol, 2,2-dimethyl-1,3-propanediol, 2-methyl-2-butyl-1,3-propanediol, 2,2-dimethyl-1,4-butanediol, 1,4-dimethylolcyclohexane, neopentyl glycol hydroxypivalate, diethylene glycol, triethylene glycol and methyldiethanolamine or aromatic-aliphatic or aromatic-cycloaliphatic diols having 8 to 30 carbon atoms, where suitable aromatic structures are heterocyclic ring systems or preferably isocyclic ring systems, such as naphthalene or, in particular, benzene derivatives, such as bisphenol A, symmetrically diethoxylated bisphenol A, symmetrically dipropoxylated bisphenol A, polyethoxylated or -propoxylated bisphenol A derivatives or bisphenol F derivatives, and mixtures of such compounds, may be advantageous.

In amounts of up to 5% by weight, based on the total weight of the alcohols aliphatic triols having 3 to 15, preferably 3 to 10, carbon atoms, such as trimethylolpropane or glycerol, the product of the reaction of such compounds with ethylene oxide and/or propylene oxide, and mixtures of such compounds, may advantageously be suitable.

The polyhydric alcohols may carry functional groups, for example neutral groups, such as siloxane groups, basic groups, such as, in particular, tertiary amino groups, or acidic groups or their salts or groups which can easily be converted into acidic groups, which are introduced via a polyhydric alcohol. Diol components carrying such groups, such as N-methyldiethanolamine, diethyl N,N-bis(hydroxyethyl) aminomethylphosphonate or 3-sulfopropyl N,N-bis(hydroxyethyl)-2-aminoacetate, or dicarboxylic acids which carry such groups and which can be used for the preparation of polyesterols, such as 5-sulfoisophthalic acid can preferably be used.

Acidic groups are, in particular, the phosphoric acid, phosphonic acid, sulfuric acid, sulfonic acid, carboxyl or amino group.

Groups which can easily be converted into acidic groups are, for example, the ester group or salts, preferably of the alkali metals, such as lithium, sodium or potassium.

6) The polyesterols described above per se, where it should be noted that molecular weights in the range from 10,000 to 2,000,000, preferably from 50,000 to 1,000,000, are obtained.

7) Polyamines, polysiloxanes and polyphosphazenes, in particular those which have already been discussed in the description of the polymer IIb2.

8) Polyetherols as described, for example, in the above discussion of the polymer IIb1 as compound (c) or in the discussion of the polyurethanes.

It is of course also possible to employ mixtures of the above polymers IIb. The copolymers IIb employed in accordance with the invention may, depending on the preparation meted, contain the monomers in a random distribution or be in the form of block copolymers.

The polymers IIa and IIb are polymerized in a conventional manner well known to the person skilled in the art, preferably by free-radical polymerization. The polymers IIa and IIb can be employed in either high molecular weight or oligomeric form or as a mixture thereof.

The proportions of the polymers IIa in the polymeric material II is generally from 1 to 100% by weight, preferably from 20 to 80% by weight, further preferably from 30 to 70% by weight. Correspondingly, the proportion of the polymer IIb in the polymeric material II is generally from 0 to 99% by weight, preferably from 20 to 80% by weight, further preferably from 30 to 70% by weight.

The present invention preferably relates to the following compositions:

Compositions as defined above in which the polymer IIa contains at least one reactive group RGa on the chain in terminal and/or lateral positions which is capable of hydrogen abstraction in the triplet-excited state at elevated temperature and/or with UV radiation, and contains at least one group RGb on the chain in terminal and/or lateral positions which is different from RGa and is coreactive with RGa, where, on average of all polymer molecules, at least one group RGa and one group RGb are present;

compositions as defined above in which the polymer IIa is a polymer or copolymer of an acrylate or methacrylate and contains reactive groups RGa containing benzophenone units and reactive groups RGb containing dihydrodicyclopentadiene units;

compositions as defined above in which the polymer IIb is selected from the group consisting of polymers and copolymers of vinyl chloride, acrylonitrile and vinylidene fluoride; copolymers of vinyl chloride and vinylidene chloride, vinyl chloride and acrylonitrile, vinylidene fluoride and hexafluoropropylene, vinylidene fluoride with hexafluoropropylene; terpolymers of vinylidene fluoride and hexafluoropropylene and a member from the group consisting of vinyl fluoride, tetrafluoroethylene and a trifluoroethylene;

compositions as defined above in which the polymer IIa is a polymer or copolymer of an acrylate or methacrylate and contains reactive groups RGa containing benzophenone units and reactive groups RGb containing dihydrodicyclopentadiene units, and the polymer IIb is a copolymer of vinylidene fluoride and hexafluoropropylene.

The compositions according to the invention may furthermore contain a plasticizer III. However, it is also possible to work without plasticizers.

If present, the proportion of the plasticizer III, based on the composition, is from 0.1 to 100% by weight, preferably from 0.5 to 50% by weight, in particular from 1 to 20% by weight.

The plasticizers III used can be aprotic solvents, preferably those which solvate Li ions, for example dimethyl carbonate, ethylmethyl carbonate, diethyl carbonate, dipropyl carbonate, diisopropyl carbonate, dibutyl carbonate, propylene carbonate; cyclic carbonates of the empirical formula $C_nH_{n+1}O_y$, where n=2 to 30, m=3 to 7, for example ethylene carbonate, 1,2-propylene carbonate, 1,3-propylene carbonate, 1,2-butylene carbonate, 1,3-butylene carbonate, 1,4-butylene carbonate and 2,3-butylene carbonate; oligoalkylene oxides, for example dibutyl ether, di-tert-butyl ether, dipentyl ether, dihexyl ether, diheptyl ether, dioctyl ether, dinonyl ether, didecyl ether, didodecyl ether, ethylene glycol dimethyl ether, ethylene glycol diethyl ether, 1-tert-butoxy-2-methoxyethane, 1-tert-butoxy-2-ethoxyethane, 1,2-dimethoxypropane, 2-methoxyethyl ether, 2-ethoxyethyl ether, diethylene glycol dibutyl ether, dimethylene glycol tert-butyl methyl ether, triethylene glycol dimethyl ether, tetraethylene glycol dimethyl ether, γ-butyrolactone and dimethylformamide; dimethyl-γ-butyrolactone, diethyl-γ-butyrolactone, γ-valerolactone, 4,5-dimethyl-1,3-dioxolan-2-one, 4,4-dimethyl-1,3-dioxolan-2-one, 4-ethyl-1,3-dioxolan-2-one, 4-methyl-5-ethyl- 1,3-dioxolan-2-one, 4,5-diethyl-1,3-dioxolan-2-one, 4,4-diethyl-1,3-dioxolan-2-one, 1,3-dioxan-2-one, 4-methyl-1,3-dioxan-2-one, 5-methyl-1,3-dioxan-2-one, 4,4-dimethyl-1,3-dioxan-2-one, 5,5- dimethyl-1,3-dioxan-2-one, 4,6-dimethyl-1,3-dioxan-2-one, 4,4,6-trimethyl-1,3-dioxan-2-one, 5,5-diethyl-1,3-dioxan-2-one, spiro-(1,3-oxa-2-cyclohexanone)-5',5',1',3'-oxacyclohexane; 4-dimethyl-ethoxysilyl-1,2-butylene carbonate; dicarboxylates of the formula $R^1OCOOR^2OCOOR^3$ ($R^1$, $R^2$ and $R^3=C_1-C_{20}$-hydrocarbons), organic esters of the formula $R^1$—$COOR^2$ ($R^1$ and $R^2=C_1-C_{20}$-hydrocarbons); hydrocarbons of the general formula $C_nH_{2n+2}$, where 7<n<50; organophosphorus compounds, in particular phosphates and phosphonates, for example trimethyl phosphate, triethyl phosphate, tripropyl phosphate, tributyl phosphate, triisobutyl phosphate, tripentyl phosphate, trihexyl phosphate, trioctyl phosphate, tris(2-ethylhexyl) phosphate, tridecyl phosphate, diethyl-n-butyl phosphate, tris(butoxyethyl) phosphate, tris(2-methoxyethyl) phosphate, tris(tetrahydrofuryl) phosphate, tris(1H,1H,5H-octafluoropentyl) phosphate, tris(1H,1-trifluoroethyl) phosphate, tris(2-(diethylamino)ethyl) phosphate, tris(methoxyethoxyethyl) phosphate, tris(methoxyethoxy)trifluorophosphazene, tris(ethoxycarbonyloxyethyl) phosphate, diethylethyl phosphonate, dipropyl propyl phosphonate, dibutyl butyl phosphonate, dihexyl hexyl phosphonate, dioctyl octyl phosphonate, ethyl dimethyl phosphonoacetate, methyl diethyl phosphonoacetate, triethyl phosphonoacetate, dimethyl 2-hydroxypropylphosphonate, diethyl 2-hydroxypropylphosphonate, dipropyl 2-hydroxypropylphosphonate, ethyl diethoxyphosphinylformate, trimethyl phosphonoacetate, tripropyl phosphonoacetate, tributyl phosphonoacetate; organic sulfur compounds, for example sulfates, sulfonates, sulfoxides, sulfones and sulfites, for example dimethyl sulfite, diethyl sulfite, glycol sulfite, dimethyl sulfone, diethyl sulfone, dipropyl sulfone, dibutyl sulfone, tetramethylene sulfone, methylsulfolane, dimethyl sulfoxide, diethyl sulfoxide, dipropyl sulfoxide, dibutyl sulfoxide, tetramethylene sulfoxide, ethyl methanesulfonate, 1,4-butanediol bis(methanesulfonate), diethyl sulfate, dipropyl sulfate, dibutyl sulfate, dihexyl sulfate, dioctyl sulfate, $SO_2ClF$; nitriles, for example acrylonitrile; dispersants, in particular having a surfactant structure, and mixtures thereof.

In addition, it is possible to use very generally suitable organic compounds, for example alkanes $C_nH_xF_y$, where n=5 to 30, x+y=2n+2; ethers $C_nH_xF_yO_z$, where n=5 to 30, x+y=2n+2, z=1 to 4; ketones $C_nH_xF_yO$, where n=5 to 30, x+y=2n; esters $C_nH_xF_yO_2$; where n=5 to 30, x+y=2n; carbonates $C_nH_xF_yO_3$, where n=5 to 30, x+y=2n; lactones $C_nH_xF_yO_2$, where n=5 to 20, x+y=2n-2; cyclic carbonates $C_nH_xF_yO_3$, where n=5 to 20, x+y=2n-2; and borates where

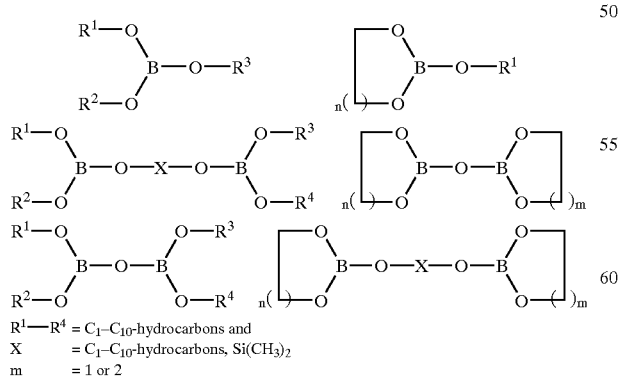

$R^1$—$R^4$ = $C_1$–$C_{10}$-hydrocarbons and
X = $C_1$–$C_{10}$-hydrocarbons, $Si(CH_3)_2$
m = 1 or 2 in particular trimethyl borate, triethyl borate, tripropyl borate, tributyl borate, trimethylene borate, 2-methyl-1,3,2-dioxaborinane, 2-ethyl-1,3,2-dioxaborinane, 2-propyl-1,3,2-dioxaborinane, 2-butyl-1,3,2-dioxaborinane, 2-phenyl-1,3,2-dioxaborinane, as plasticizer V.

Furthermore, at least one ester of the formulae (E1) to (E5), as shown below, can be used as plasticizer (V):

 (E1)

 (E2)

 (E3)

 (E4)

 (E5)

where $R^1$, $R^2$, $R^3$ and $R^4$ are identical or different and are each, independently of one another, a linear or branched $C_1$- to $C_4$-alkyl group, $(-CH_2-CH_2-O)_n-CH_3$, where n=1 to 3, a $C_3$- to $C_6$-cycloalkyl group, an aromatic hydrocarbon group, which may in turn be substituted, with the proviso that at least one of the groups $R^1$, $R^2$, $R^3$ and $R^4$ is $(-CH_2-CH_2'O)_n-CH_3$, where n=1 to 3.

Of the abovementioned esters of the formulae (E1) to (E5), the phosphates of the formula (E3) are preferably employed.

Examples of the groups $R^1$, $R^2$ and—if present—$R^3$ and/or $R^4$ are the methyl, ethyl, n- and isopropyl; n- and tert-butyl, cyclopentyl, cyclohexyl and benzyl groups, and $(-CH_2-CH_2-O)_n-CH_3$ where n=1 to 3, but where, as already mentioned above, it must be ensured that at least one of the groups $R^1$, $R^2$, $R^3$ and $R^4$ is $(-CH_2-CH_2-O)_n-CH_3$, where n=1 to 3, preferably 1 or 2.

Further preference is given to the use of esters of the formulae (E1) to (E5), in which $R^1$, $R^2$ and—if present—$R^3$ and/or $R^4$ are identical and are —$CH_2$—$CH_2O$—$CH_3$ or $(-CH_2-CH_2-O)_2-CH_3$, where the corresponding phosphates are again preferred here.

Examples of particularly preferred compounds are the compounds of the formulae (E1a) to (E5a):

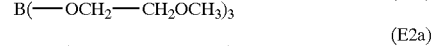 (E1a)

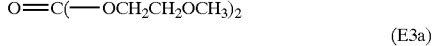 (E2a)

 (E3a)

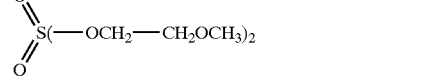 (E4a)

and

 (E5a)

With respect to their properties, the esters described herein are extremely suitable as plasticizers in the foils and generally have a viscosity at room temperature of $\leq 10$ mPas, preferably $\leq 5$ mPas, in particular $\leq 3$ mPas. They have boiling points of generally approximately 200° C. or above, preferably approximately 250° C. or above, in particular approximately 300° C. or above, in each case measured at atmospheric pressure, and, at the temperatures of from about −50° C. to 150° C. which occur during their use, have a sufficiently low vapor pressure of from approximately $10^{-5}$ to approximately $10^0$. Due to their boiling points, they can be distilled and can thus be obtained in high purity in their preparation. In addition, these esters are liquid over a broad temperature range at atmospheric pressure, generally still being liquid down to a temperature of approximately −30° C., preferably down to approximately −40° C. The esters described here can be employed as solvents in electrolyte systems for rechargeable Li ion batteries at at least approximately 80° C., preferably at at least approximately 120° C., further preferably at at least approximately 150° C.

The esters used according to the invention can of course also be employed as a mixture with the abovementioned plasticizers.

Preference is given to solvent combinations which have a sufficiently low viscosity, are capable of strongly solvating the ions of the conductive salts, are liquid over a broad temperature range and are sufficiently electrochemically and chemically stable and hydrolysis-resistant.

The esters used in accordance with the invention are prepared by conventional processes, as described, for example, in K. Mura Kami in Chem. High Polymers (Japan), 7, pp. 188–193 (1950) and in H. Steinberg Organoboron Chemistry, chapter 5, J. Wiley & Sons, N.Y. 1964. The preparation generally starts from the acids, acid anhydrides or chlorides on which the esters are based, for example boric acid, $C(O)Cl_2$, $POCl_3$, $SO_2Cl_2$ and $SiCl_4$, which are reacted with the corresponding monohydric or polyhydric alcohols or etherols in a known manner.

The compositions according to the invention can be dissolved or dispersed in an inorganic or organic, preferably organic, liquid diluent, where the mixture according to the invention should preferably have a viscosity of from 100 to 50,000 mPas, and subsequently applied to a support material in a manner known per se, such as spray coating, pouring, dipping, spin coating, roller coating, letterpress printing, intaglio printing, planographic printing or screen printing. The further processing can be carried out in the usual manner, for example by removal of diluent and curing of the mixture.

Suitable organic diluents are aliphatic ethers, in particular tetrahydrofuran and dioxane, hydrocarbons, in particular hydrocarbon mixtures, such as benzine, toluene and xylene, aliphatic esters, in particular ethyl acetate and butyl acetate, and ketones, in particular acetone, ethyl methyl ketone and cyclohexanone, and DMF and NMP. It is also possible to employ combinations of such diluents.

Suitable support materials are the materials usually used for electrodes, preferably metals, such as aluminum and copper. It is also possible to use temporary interim supports, such as foils, in particular polyester foils, such as polyethylene terephthalate foils. Such foils may advantageously be provided with a release coating, preferably of polysiloxanes.

The solid electrolytes and separators can likewise be produced thermoplastically, for example by injection molding, melt casting, pressing, compounding or extrusion, if desired with a subsequent calendering step of the mixture according to the invention.

After film formation of the mixture according to the invention, volatile components, such as solvents or plasticizers, can be removed.

The crosslinking of the composition according to the invention can be carried out in a manner known per se, for example by irradiation with ionic or ionizing radiation, electron beams, preferably with an acceleration voltage of between 20 and 2000 kV and a radiation dose of between 5 and 50 Mrad, UV or visible light, it being advantageous to add an initiator, such as benzyl dimethyl ketal or 1,3,5-trimethylbenzoyltriphenylphosphine oxide, in a conventional manner in maximum amounts of, in particular, 1% by weight, based on the polymer IIa, and to carry out the crosslinking within, in general, from 0.5 to 15 minutes; by thermal crosslinking by free-radical polymerization, preferably at temperatures of above 60° C., in which case an initiator, such as azobisisobutyronitrile, may advantageously be added in maximum amounts of, in general, 5% by weight, preferably from 0.05 to 1% by weight, based on the polymer IIa; by electrochemically induced polymerization; or by ionic polymerization, for example by acid-catalyzed cationic polymerization, where suitable catalysts are primarily acids, preferably Lewis acids, such as $BF_3$, or in particular $LiBF_4$ or $LiPF_6$. Catalysts containing lithium ions, such as $LiBF_4$ and $LiPF_6$, can advantageously remain in the solid electrolyte or separator as conductive salt.

The crosslinking described above can, but need not, be carried out under an inert gas.

If the composition according to the invention is to be employed as solid electrolyte or separator in an electrochemical cell, a lithium cation-containing compound which is capable of dissociation, a so-called conductive salt, and, if desired, further additives, such as, in particular, organic solvents, a so-called electrolyte, are incorporated.

Some or all of these substances are admixed with the composition during production of the layer or introduced into the layer after its production.

Conductive salts which can be used are the generally known conductive salts described, for example, in EP-A 0 096 629. The conductive salt preferably employed according to the invention is $LiPF_6$, $LiBF_4$, $LiClO_4$, $LiAsF_6$, $LiCF_3SO_3$, $LiC(CF_3SO_2)_3$, $LiN(CF_3SO_2)_2$, $LiN(SO_2C_nF_{2n+1})_2$, $LiC[(C_nF_{2n-1})SO_2]_3$, $Li(C_nF_{2n+1})SO_2$, where n is in each case from 2 to 20, $LiN(SO_2F)_2$, $LiAlCl_4$, $LiSiF_6$, $LiSbF_6$, $(RSO_2)_nXli$ ($_nX=_1O$, $_1S$, $_2N$, $_2P$, $_3C$, $_3Si$; $R=CmF_{2m+1}$ where m=0–10 or $C_1$–$C_{20}$-hydrocarbons), Li imide salts, or a mixture of two or more thereof, where the conductive sot employed is preferably $LiPF_6$.

Suitable organic electrolytes are the compounds discussed above under "plasticizers", preference being given to the conventional organic electrolytes, preferably esters, such as ethylene carbonate, -propylene carbonate, dimethyl carbonate and diethyl carbonate, or mixtures of such compounds.

Solid electrolytes, separators and/or electrodes according to the invention which are suitable for Electrochemical cells should advantageously have a thickness of from 5 to 500 $\mu$m, preferably from 10 to 500 $\mu$m, further preferably from 10 to 200 $\mu$m, in particular from 20 to 100 $\mu$m.

The compositions according to the invention can be employed in electrochemical cells as the only solid electrolyte and/or separator and/or electrode or as a mixture with other solid electrolytes, separators and/or electrodes, the use as solid electrolyte being preferred.

Furthermore, when used as solid electrolyte and/or separator, the composition according to the invention can also be combined with a conventional separator, it being possible, in accordance with the invention, to employ all conventional separators.

Particular mention should be made of the following:

separators based on microporous polyolefin foils, as commercially available, for example, under the trade names Celgard® and Hipore® and described, inter alia, in EP-A 0 718 901 and EP-B 0 715 364, both of which are incorporated by way of reference in their full content in the context of the present application; polyethylene and polypropylene foils and foils containing blends of polyethylene or polypropylene with other polymers are likewise readily usable;

microporous polytetrafluoroethylene (PTFE) foils from the Goretex company, as described, for example, in EP-A 0 798 791, which is likewise incorporated by way of reference in the context of the present application;

fleeces, fibers and non-woven textile composites, so-called "nonwovens", all of which can be produced using fibrous polymer materials, for example polyolefin, polyamide and polyester fibers;

foils available under the tradename Nafion®;

foils based on a copolymer of vinylidene fluoride and hexafluoropropene, as described, for example, in U.S. Pat. Nos. 5,540,741 and 5,478,668;

filler-containing homopolymers, block polymers and copolymers obtainable by extrusion and prepared from
(a) olefinic hydrocarbons, for example ethylene, propylene, butylene, isobutene, propene, hexene or higher homologs, butadiene, cyclopentene, cyclohexene, norbornene or vinylcyclohexane;
(b) aromatic hydrocarbons, for example styrene and methylstyrene;
(c) acrylic acid or methacrylic acid, such as methyl, ethyl, propyl, isopropyl, butyl, isobutyl, hexyl, octyl, decyl, dodecyl, 2-ethylhexyl, cyclohexyl, benzyl, trifluoromethyl, hexafluoropropyl or tetrafluoropropyl acrylate or methacrylate;
(d) acrylonitrile, methacrylonitrile, N-methylpyrrolidone, N-vinylimidazole or vinyl acetate;
(e) vinyl ethers, for example methyl, ethyl, propyl, isopropyl, butyl, isobutyl, hexyl, octyl, dexyl, dodecyl, 2-ethylhexyl, cyclohexyl, benzyl, trifluoromethyl, hexafluoropropyl or tetrafluoropropyl vinyl ether;
(f) halogen-containing olefinic compounds, such as vinyl chloride, vinyl fluoride, vinylidene fluoride, vinylidene chloride, hexafluoropropene, trifluoropropene, 1,2-dichloroethene, 1,2-difluoroethene or tetrafluoroethene, where the fillers used in these polymers are solids (Ia) used in accordance with the invention; extruder foils of this type are described in detail with respect to their composition and production in DE-A 197 13 072.0.

To produce a composite separator/solid electrolyte of this type, at least one first separator layer including the composition according to the invention is combined with at least one second separator layer including a conventional separator, as defined above, it being possible to use, in accordance with the invention, all known processes for combining such layers. Thus, the application of the first layer to the second layer can be carried out by pressureless processes, for example casting or knife coating of the starting material for the first layer and by processing methods under pressures for example extrusion, lamination, in particular hot lamination, calendering or pressing. The composite elements produced in this way can be crosslinked or cured by radiation, electrochemically or thermally. In addition, the starting material for the at least first layer can also firstly be fully or partially thermally crosslinked or cured and subsequently, as described above, combined with the second layer used in accordance with the invention with or without pressure. If prefabricated foils, ie. the at least one first layer in the form of a foil and the conventional separator in the form of a foil, are to be combined, this is preferably carried out by lamination, generally at temperatures in the range from approximately 100 to approximately 160° C., preferably from approximately 115 to approximately 140° C. (hot lamination), where the precise temperatures used in each case depend, id particular, on the conventional separator used in each case. For example, slighty higher temperatures can be employed when polypropylene films are used than when polyethylene films are used. The composition of the first layer can also be fully or partially in crosslinked form during production of the composite element by lamination, and the composite element obtained after lamination can, if necessary, be crosslinked again or, however, employed directly without post-crosslinking.

When the composite separator/solid electrolyte obtained is used as separator/solid electrolyte in an electrochemical cell, the composite separator/solid electrolyte is combined with conventional anodes and cathodes. In addition, a lithium cation-containing compound which is capable of dissociation, a so-called conductive salt, and, if desired, farther additives, such as, in particular, organic solvents, a so-called electrolyte, are incorporated. Some or all of the last-mentioned substances are admixed during production of the composite separator/solid electrolyte according to the invention or introduced after production thereof.

The conductive salts used can be the generally known conductive salts described above.

The present invention furthermore relates to a composite element which can be used, in particular, in electrochemical cells, particularly in the form of a foil, further preferably in the form of a foil having an overall thickness of from 15 to 1500 $\mu$m, in particular having an overall thickness of from 50 to 500 $\mu$m, comprising at least one first layer containing a composition defined above which includes a compound Ib or a compound Ic, and at least one second layer containing a composition defined above which includes a solid Ia and contains no compounds Ic and lb. This composite element can also be combined with conventional electrodes, for example an anode made from graphite. The first layer defined above then contains a compound Ib giving the following element:

Anode (conventional)/second layer/first layer (separator) (cathode)

The present invention furthermore describes a process for the production of a composite element of this type which comprises the following steps:

(I) Production of at least one first layer as defined above;
(II) production of at least one second layer as defined above; and
(III) subsequent combination of the at least one first layer with the at least one second layer by a conventional coating process.

The at least one second layer is preferably produced on a temporary support. Use can be made here in accordance with the invention of the temporary supports usually used, for example a release film of a polymer or a paper, preferably coated, for example a siliconized polyester film. However, it is also possible to produce this second layer on a permanent support, for example a dissipation electrode, or, however, even entirely without a support.

The combination or production of the layers defined above is carried out by unpressurized processes for coating or production of films, for example casting or knife coating, or by processing methods under pressure, for example extrusion, lamination, preferably hot lamination, calendering or pressing. If desired, the composite element produced in this way can be crosslinked or cured by radiation, electrochemically or thermally.

As can be seen from the above, it is thus readily possible to provide a composite element having the constituents release film/separator (second layer)/electrode (first layer).

It is furthermore possible, by double-sided coating, to provide a composite element having the constituents anode/separator/cathode.

In this case, the procedure is as follows, for example:

Firstly, a first compound Ic, for example graphite, conductive black, a polymeric material II, a conductive salt and a plasticizer, for example propylene carbonate, are mixed with one another, and the resultant mixture is cast onto a dissipation electrode and subsequently irradiated by UV light (component 1). A cathode material, for example $LiMn_2O_4$, is subsequently applied to a dissipation electrode coated with conductive black, and a mixture of the composition according to the invention which contains a solid Ia and contains no compounds Ib and Ic, a conductive salt and a plasticizer is cast thereon. This composite is likewise subsequently irradiated by UV light (component 2). By combining the two components described above, a composite element is obtained which can be used, in combination with any desired solid and/or liquid electrolyte, as electrochemical cell.

A solid electrolyte/anode or solid electrolyte/cathode or even cathode/solid electrolyte/anode composite can be produced without further additives by laminating the separator foil and the anode foil and/or cathode foil together at temperatures of >80° C. It is readily possible here, for example, to laminate a composition according to the invention which contains a solid Ia onto a conventional anode or cathode, giving an anode or cathode/solid electrolyte (separator) composite, which can then in turn be combined with a conventional cathode or anode.

An anode/separator/cathode composite element as described above can also be produced without using a support or the dissipation electrodes since the composite element obtained, consisting of a first layer and a second layer as defined above, has a mechanical stability which is adequate for use in electrochemical cells.

The composition according to the invention thus enables the following configurations:

foil production or further processing, for example casting and lamination. The solid electrolyte/separator used can of course also be the composite separator/solid electrolyte described above.

Composite elements of this type can be filled with an electrolyte and conductive salt either before combination or preferably after combination of the layers, if desired after contacting with suitable dissipation electrodes, for example a metal foil, and even after introduction of the composite element into a battery casing, where the special microporous structure of the layers enabling take-up of the electrolyte and conductive salt and expulsion of the air in the pores when the mixture according to the invention is used, in particular due to the presence of the solid defined above in the separator and possibly also in the electrodes. The filling can be carried out at temperatures of from 0° C. to approximately 100° C., depending on the electrolyte used.

The electrochemical cells according to the invention can be used, in particular, as automotive, equipment or flat batteries.

As evident from the above, the present invention also relates to the use of the composition according to the invention or of the composite element described above for the production of a solid electrolyte, a separator, an electrode, in a sensor, an electrochromic window, a display, a capacitor, an ion-conducting foil or on-board battery, battery for static applications, equipment battery or battery for electric drive, and a solid electrolyte, a separator, an electrode, a sensor, an electrochromic window, a display, a capacitor, an ion-conducting foil or on-board battery, battery for static applications, equipment battery or battery for electric drive, each of which contain the mixture according to the invention or the composite element described above.

The invention furthermore relates to an electrochemical cell comprising a solid a electrolyte, separator or electrode, as defined above, or a combination of two or more thereof, and to the use of the electrochemical cells defined above as automobile batteries, equipment batteries or flat batteries.

The present invention will now be explained with reference to some examples.

FIG. 1 here shows the result of cycling (voltage 4.15 V) the electrochemical cells obtained in accordance with Example 1.

Preparation Example 1 (PA1)

Firstly, 800 g of xylene were warmed to 85° C. A feed I consisting of a mixture of

| Cathode | Solid electrolyte/separator | Anode |
|---|---|---|
| Conventional | Composition according to the invention | Conventional |
| Composition according to the invention | Composition according to the invention | Composition according to the invention |
| Composition according to the invention | Composition according to the invention | Conventional |
| Conventional | Composition according to the invention | Composition according to the invention |
| Conventional | Conventional | Composition according to the invention |
| Composition according to the invention | Conventional | Conventional |

The composite element configured in this way is then produced in the same way as described above for a molding according to the invention using conventional methods of 100 g of lauryl acrylate,
300 g of dihydrodicyclopentadienyl acrylate,
120 g of glycidyl methacrylate, 480 g of ethylhexyl acrylate and 2 g of mercaptomethanol, and a feed II consisting of 30 g of Wako V 59 (azo initiator V 59) and 200 g of xylene were then started simultaneously.

Feed I was introduced into the reactor over the course of 1.5 hours and feed II over the course of 2 hours. During this operation, the temperature was kept at between 80 and 90° C. The mixture was then allowed to react further for 3 hours at 90° C.

A mixture consisting of 166 g of 4-hydroxybenzophenone and 0.83 g of dimethylaminopyridine was then added The mixture was allowed to react for a further 2 to 3 hours until an epoxide value of <0.01 had been reached.

Preparation Example 2 (PA2)

Firstly, 800 g of xylene were warmed to 85° C. A feed I consisting of 232.5 g of lauryl acrylate, 232.5 g of dihydrodicyclopentadienyl acrylate, 93 g of glycidyl methacrylate and 442 g of ethylhexyl acrylate and a feed II consisting of 30 g of Wako V 59 (azo initiator V 59) and 200 g of xylene were introduced into the reactor simultaneously over the course of 1.5 hours (feed I) and over the course of 2 hours (feed II). During this operation, the temperature was kept at between 80 and 90° C.

The mixture was then allowed to react further for 3 hours at 90° C. A mixture consisting of 128.65 g of 4-hydroxybenzophenone and 0.65 g of dimethylaminopyridine, and 128.65 g of xylene was then added. The mixture was allowed to react for a further 2 to 3 hours until an epoxide value of <0.01 had been reached.

EXAMPLE 1

Firstly, 64 g of a solution of 6 g of a vinylidene fluoride-hexafluoropropylene copolymer (Kynarflex® 2801, ELF-Atochem) in toluene/methyl ethyl ketone 7.5:50 and a solution of 4.6 g of the PA1 prepared in accordance with Preparation Example 1 in xylene were added. 1.7 g of tris(2-ethylhexyl) phosphate were then added.

The resultant composition was subsequently knife-coated onto a support material at 50° C., the solvents were removed within 10 minutes, and the dried coating was peeled off, giving a film with a thickness of approximately 23 µm. This was photocrosslinked by exposure for 5 minutes at a distance of 5 cm under a field from superactinic fluorescent tubes (TL 09, Philips).

The resultant film was used as solid electrolyte and combined with $LiCoO_2$ as cathode and graphite as anode to give a circular sandwich cell. Using $LiPF_6$ as conductive salt and a 1:1 mixture of ethylene carbonate and diethylene carbonate as liquid electrolyte, an electrochemical cell was obtained which was cycled with application of a voltage of 4.15 V.

The specific battery data achieved using this cell were found to be the following:

Battery Test

Cathode area: 1 $cm^2$

Anode area: 1 $cm^2$

Weight per unit area of cathode: 263.6 $g/m^2$

Electrolyte: 1M $LiPF_6$/ethylene carbonate (EC): diethylene carbonate (DEC)=1:1

The results of this cycling are shown in FIG. 1. As can be seen, this cell had a specific capacitance at the cathode of 86 mAh/g in, for example, the $5^{th}$ discharge cycle (see Table 1).

TABLE 1

| Cycle No. | Half cycle | Current density [mA/$cm^2$] | Specific capacitance [mAh/g] Charging | Specific capacitance [mAh/g] Discharging |
|---|---|---|---|---|
| 1 | c (Li out) | 0.5 | 97.1 | |
|   | d (Li in)  | −1.0 |     | 94.3 |
| 2 | c (Li out) | 0.5 | 93.8 | |
|   | d (Li in)  | −1.0 |     | 90.9 |
| 3 | c (Li out) | 0.5 | 92.0 | |
|   | d (Li in)  | −1.0 |     | 91.5 |
| 4 | c (Li out) | 0.5 | 91.1 | |
|   | d (Li in)  | −1.0 |     | 89.0 |
| 5 | c (Li out) | 0.5 | 88.4 | |
|   | d (Li in)  | −1.0 |     | 86.0 |
| 6 | c (Li out) | 0.5 | 85.0 | |
|   | c (Li out) | 0.25 | 5.3 | |
|   | d (Li in)  | −3.0 |     | 23.1 |
| 7 | c (Li out) | 1.0 | 16.2 | |
|   | d (Li in)  | −2.0 |     | 40.2 |
| 8 | c (Li out) | 1.0 | 37.5 | |
|   | d (Li in)  | −2.0 |     | 36.7 |
| 9 | c (Li out) | 1.0 | 35.6 | |
|   | d (Li in)  | −2.0 |     | 32.7 |
| 10 | c (Li out) | 1.0 | 31.8 | |
|    | d (Li in)  | −2.0 |     | 28.5 |
| 11 | c (Li out) | 1.0 | 27.6 | |
|    | d (Li in)  | −2.0 |     | 24.5 |
| 12 | c (Li out) | 0.5 | 31.9 | |
|    | c (Li out) | 0.25 | 4.8 | |

EXAMPLE 2

A composition according to the invention was prepared in the same way as in Example 1, but this time a solution of 5 g of PA2 as a 50% strength solution in xylene was used. Furthermore, 1.7 g of tris(2-ethylhexyl) phosphate were used.

This composition was used to produce, analogously to Example 1, a film with a thickness of 29 µm. This film was photocrosslinked by exposure for 5 minutes as described in Example 1. This film was used analogously to Example 1 to give a sandwich-like cell.

This was tested in the same way as the cell obtained in accordance with Example 1.

The specific battery data achieved using this cell were found to be the following:

Battery Test

Cathode area: 1 $cm^2$

Anode area: 1 $cm^2$

Weight per unit area of cathode: 270 $g/m^2$

Electrolyte: 1M $LiPF_6$/ethylene carbonate (EC): diethylene carbonate (DEC)=1:1

Figure 2:
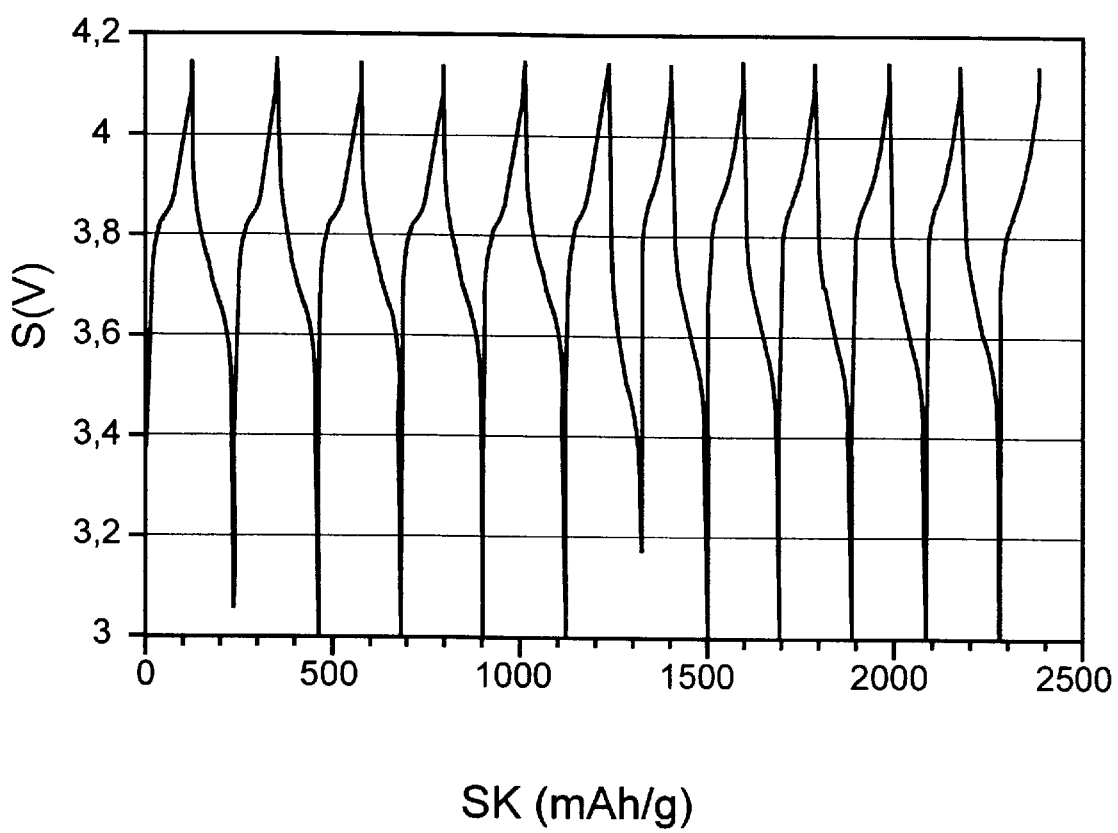
FIG. 2 shows the results of cycling the cell in accordance with Example 2.

The results of this cycling are shown in FIG. 2. As can be seen, this cell had a specific capacitance at the cathode of 109 mAh/g in, for example, the $5^{th}$ discharge cycle (see Table 2).

TABLE 2

| Cycle No. | Half cycle | Current density [mA/cm$^2$] | Specific capacitance [mAh/g] Charging | Specific capacitance [mAh/g] Discharging |
|---|---|---|---|---|
| 1 | c (Li out) | 0.5 | 124.0 | |
|   | d (Li in)  | −1.0 |      | 113.2 |
| 2 | c (Li out) | 0.5 | 115.2 | |
|   | d (Li in)  | −1.0 |      | 111.8 |
| 3 | c (Li out) | 0.5 | 113.2 | |
|   | d (Li in)  | −1.0 |      | 110.5 |
| 4 | c (Li out) | 0.5 | 111.4 | |
|   | d (Li in)  | −1.0 |      | 109.3 |
| 5 | c (Li out) | 0.5 | 110.6 | |
|   | d (Li in)  | −1.0 |      | 108.9 |
| 6 | c (Li out) | 0.5 | 108.8 | |
|   | c (Li out) | 0.25 | 5.5 | |
|   | d (Li in)  | −3.0 |      | 93.1 |
| 7 | c (Li out) | 1.0 | 84.0 | |
|   | d (Li in)  | −2.0 |      | 98.7 |
| 8 | c (Li out) | 1.0 | 98.5 | |
|   | d (Li in)  | −2.0 |      | 98.1 |
| 9 | c (Li out) | 1.0 | 98.9 | |
|   | d (Li in)  | −2.0 |      | 98.2 |
| 10 | c (Li out) | 1.0 | 99.4 | |
|    | d (Li in)  | −2.0 |      | 98.6 |
| 11 | c (Li out) | 1.0 | 99.8 | |
|    | d (Li in)  | −2.0 |      | 98.7 |
| 12 | c (Li out) | 0.5 | 106.1 | |
|    | c (Li out) | 0.25 | 5.0 | |

We claim:

1. A composition comprising:
   (a) from 0 to less than 1% by weight of a pigment (I) having a primary particle size of from 5 nm to 100 μm which is a solid (Ia) or a compound (Ib) which acts as cathode material in electrochemical cells or a compound (Ic) which acts as anode material in electrochemical cells or a mixture of the solid (Ia) with the compound (Ib) or the compound (Ic),
   (b) more than 99 to 100% by weight of a polymeric material (II) which comprises:
      (IIa) from 1% up to, but not including 100% by weight of a polymer or copolymer (IIa) containing reactive groups (RG) on the chain in terminal and/or lateral positions which are capable of cross linking reactions in the presence of heat and/or with UV radiation where the polymer or copolymer (IIa) contains at least one reactive group (RGa) on the chain, in terminal and/or lateral positions which is capable of hydrogen abstraction in the triplet-excited state at elevated temperature and/or with UV radiation, and contains at least one group (RGb) on the chain, in terminal and/or lateral positions which is different from (RGa) and is coreactive with (RGa), where, on average of all polymer molecules, at least one group (RGa) and one group (RGb) are present, and
      (IIb) from 99% down to, but not including 0% by weight of at least one thermoplastic and ion-conducting polymer or copolymer (IIb) which contains no reactive groups (RG).

2. A composition as claimed in claim 1, where the polymer (IIa) is a polymer or copolymer of an acrylate or methacrylate and contains reactive groups (RGa) containing benzophenone units and reactive groups (RGb) containing dihydrodicyclopentadiene units.

3. A composition as claimed in claim 1, where the polymer (IIb) is selected from the group consisting of polymers and copolymers of vinyl chloride, acrylonitrile and vinylidene fluoride; copolymers of vinyl chloride and vinylidene chloride, vinyl chloride and acrylonitrile, vinylidene fluoride and hexafluoropropylene, and vinylidene fluoride with hexafluoropropylene; terpolymers of vinylidene fluoride and hexafluoropropylene and a member from the group consisting of vinyl fluoride, tetrafluoroethylene and a trifluoroethylene; polyurethanes, poly-THF, polyethylene oxide, solvent-soluble polyolefins and copolymers thereof, polyvinylpyrrolidone and polyacrylates which are different from the polymer (IIa).

4. A composition as claimed in claim 1, where the polymer (IIa) is a polymer or copolymer of an acrylate or methacrylate and contains reactive (RGa) containing benzophenone units and reactive groups (RGb) containing dihydrodicyclopentadiene units and the polymer (IIb) is a copolymer of vinylidene fluoride and hexafluoropropylene.

5. A composite element comprising at least one first layer containing a composition as claimed in claim 1, which includes a compound (Ib) or a compound (Ic), and at least one second layer containing a composition as claimed in claim 1 which includes a solid (Ia) and contains no compounds (Ic) and (Ib).

6. A solid electrolyte, separator, electrode, sensor, electrochromic window, display, capacitor, ion-conducting foil or on-board battery, a battery for static applications, an equipment battery or a battery for electric drive, in each case containing a composition as claimed in claim 1.

7. A solid electrolyte, separator, electrode, sensor, electrochromic window, display, capacitor, ion-conducting foil or on-board battery, a battery for static applications, an equipment battery or a battery for electric drive, in each case containing a composite element as claimed in claim 5.

8. An electrochemical cell comprising a solid electrolyte, separator or electrode as claimed in claim 6 or combination of two or more thereof.

9. An electrochemical cell comprising a solid electrolyte, separator or electrode as claimed in claim 7 or a combination of two or more thereof.

* * * * *

Disclaimer 6,475,663—Helmut Mohwald, Annweiler; Gerhard Dotter; Rainer Blum, both of Ludwigshafen; Peter Keller, Spiesen-Elversber; Stephan Bauer, Hochdorf-Assenheim; Bernd Bronstert, Otterstadt, all of (DE). COMPOSITIONS SUITABLE FOR ELECTRONCHEMICAL CELLS. Patent dated November 5, 2002. Disclaimer filed March 1, 2004, by the assignee, BASF Aktiengesellschaft.

The term of this patent shall not extend beyond the expiration date of application serial No. 09/674,541.

*(Official Gazette, June 15, 2004)*